(12) United States Patent
Reichen et al.

(10) Patent No.: US 9,078,771 B2
(45) Date of Patent: Jul. 14, 2015

(54) TRIAL IMPLANT ASSEMBLY

(75) Inventors: Marc Reichen, West Chester, PA (US);
David Chow, West Chester, PA (US); K. Daniel Riew, St. Louis, MO (US); Kurt Schmura, West Chester, PA (US); Christopher Bonner, West Chester, PA (US); David Gerber, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 446 days.

(21) Appl. No.: 12/760,679

(22) Filed: Apr. 15, 2010

(65) Prior Publication Data

US 2010/0280620 A1 Nov. 4, 2010

Related U.S. Application Data

(60) Provisional application No. 61/169,444, filed on Apr. 15, 2009.

(51) Int. Cl.
*A61F 2/44* (2006.01)
*A61F 2/46* (2006.01)
*A61F 2/30* (2006.01)

(52) U.S. Cl.
CPC .............. *A61F 2/4684* (2013.01); *A61F 2/442* (2013.01); *A61F 2/4611* (2013.01); *A61F 2002/30553* (2013.01); *A61F 2250/0008* (2013.01)

(58) Field of Classification Search
CPC ............................. A61F 2/4684; A61F 2/4611
USPC ............. 623/17.11–17.16; 606/86 A, 99, 102
See application file for complete search history.

(56) References Cited

U.S. PATENT DOCUMENTS

| | | | |
|---|---|---|---|
| 5,314,477 A | 5/1994 | Marnay | |
| 6,524,318 B1 * | 2/2003 | Longhini et al. | 606/86 R |
| 6,582,437 B2 * | 6/2003 | Dorchak et al. | 606/90 |
| 6,635,060 B2 * | 10/2003 | Hanson et al. | 606/79 |
| 6,755,841 B2 * | 6/2004 | Fraser et al. | 606/99 |
| 7,169,182 B2 * | 1/2007 | Errico et al. | 623/17.15 |
| 7,192,447 B2 * | 3/2007 | Rhoda | 623/17.11 |
| 7,361,193 B2 * | 4/2008 | Frey et al. | 623/17.16 |
| 7,491,204 B2 * | 2/2009 | Marnay et al. | 606/86 R |
| 7,776,047 B2 * | 8/2010 | Fanger et al. | 606/96 |

(Continued)

FOREIGN PATENT DOCUMENTS

| | | |
|---|---|---|
| DE | 10 2004 043 995 | 3/2006 |
| WO | WO 03/077808 | 9/2003 |

(Continued)

OTHER PUBLICATIONS

International Patent Application No. PCT/US2010/031148: International Search Report dated Aug. 25, 2010, 8 pages.

*Primary Examiner* — Eduardo C Robert
*Assistant Examiner* — Jacqueline Johanas
(74) *Attorney, Agent, or Firm* — Baker & Hostetler LLP

(57) ABSTRACT

A trial implant assembly is provided that includes a threaded shaft having exterior threading adjacent a distal end and a trial implant that includes a trial base having an interiorly threaded through hole couplable to the distal end of the shaft and a trial head having a superior endplate and an inferior endplate and a support connecting the superior endplate to the inferior endplate. A variety of visualization windows are provided through the trial implant as well as a variety of mechanically adjustable stops to prevent over insertion of the trial head within the intervertebral disc space.

37 Claims, 33 Drawing Sheets

(56) References Cited

U.S. PATENT DOCUMENTS

| | | | |
|---|---|---|---|
| 7,887,595 B1* | 2/2011 | Pimenta | 623/17.16 |
| 7,947,044 B2* | 5/2011 | Ullrich et al. | 606/79 |
| 7,967,863 B2* | 6/2011 | Frey et al. | 623/17.11 |
| 7,998,212 B2* | 8/2011 | Schwab et al. | 623/17.16 |
| 8,172,848 B2* | 5/2012 | Tomko et al. | 606/87 |
| 8,298,235 B2* | 10/2012 | Grinberg et al. | 606/86 A |
| 8,579,911 B2* | 11/2013 | Dudasik | 606/99 |
| 8,613,772 B2* | 12/2013 | Bray et al. | 623/17.16 |
| 2003/0114931 A1* | 6/2003 | Lee et al. | 623/17.11 |
| 2004/0054412 A1* | 3/2004 | Gerbec et al. | 623/17.15 |
| 2004/0097932 A1* | 5/2004 | Ray et al. | 606/61 |
| 2004/0117020 A1* | 6/2004 | Frey et al. | 623/17.11 |
| 2004/0122518 A1* | 6/2004 | Rhoda | 623/17.11 |
| 2004/0153156 A1* | 8/2004 | Cohen et al. | 623/17.13 |
| 2004/0204717 A1* | 10/2004 | Fanger et al. | 606/96 |
| 2004/0215198 A1* | 10/2004 | Marnay et al. | 606/86 |
| 2004/0267274 A1* | 12/2004 | Patel et al. | 606/96 |
| 2005/0043740 A1* | 2/2005 | Haid et al. | 606/90 |
| 2005/0159819 A1* | 7/2005 | McCormack et al. | 623/17.16 |
| 2006/0084986 A1* | 4/2006 | Grinberg et al. | 606/61 |
| 2006/0217806 A1 | 9/2006 | Peterman et al. | |
| 2007/0027544 A1* | 2/2007 | McCord et al. | 623/17.11 |
| 2007/0032872 A1* | 2/2007 | Simonton et al. | 623/17.11 |
| 2007/0118145 A1* | 5/2007 | Fischer et al. | 606/99 |
| 2007/0123985 A1* | 5/2007 | Errico et al. | 623/17.11 |
| 2007/0208345 A1* | 9/2007 | Marnay et al. | 606/61 |
| 2007/0209222 A1 | 9/2007 | Fischer et al. | |
| 2007/0282441 A1 | 12/2007 | Stream et al. | |
| 2007/0282444 A1* | 12/2007 | Lo et al. | 623/17.11 |
| 2008/0082169 A1 | 4/2008 | Gittings et al. | |
| 2008/0103598 A1* | 5/2008 | Trudeau et al. | 623/17.16 |
| 2008/0269756 A1* | 10/2008 | Tomko et al. | 606/87 |
| 2008/0269806 A1* | 10/2008 | Zhang et al. | 606/286 |
| 2008/0306598 A1* | 12/2008 | Hansen et al. | 623/17.16 |
| 2009/0125033 A1* | 5/2009 | Hushka et al. | 606/99 |
| 2009/0149960 A1* | 6/2009 | Hushka et al. | 623/17.16 |
| 2009/0177195 A1* | 7/2009 | Rawles et al. | 606/53 |
| 2010/0076443 A1* | 3/2010 | Bertagnoli et al. | 606/87 |
| 2010/0106250 A1* | 4/2010 | Abdou | 623/17.11 |
| 2010/0217395 A1* | 8/2010 | Bertagnoli et al. | 623/17.16 |
| 2011/0015685 A1* | 1/2011 | Fanger et al. | 606/86 A |
| 2011/0092976 A1* | 4/2011 | Rawles et al. | 606/83 |
| 2011/0230970 A1* | 9/2011 | Lynn et al. | 623/17.16 |

FOREIGN PATENT DOCUMENTS

| | | |
|---|---|---|
| WO | WO 2006/033067 | 3/2006 |
| WO | WO 2006/130460 | 12/2006 |
| WO | WO 2007/016247 | 2/2007 |
| WO | WO 2008/034140 | 3/2008 |

* cited by examiner

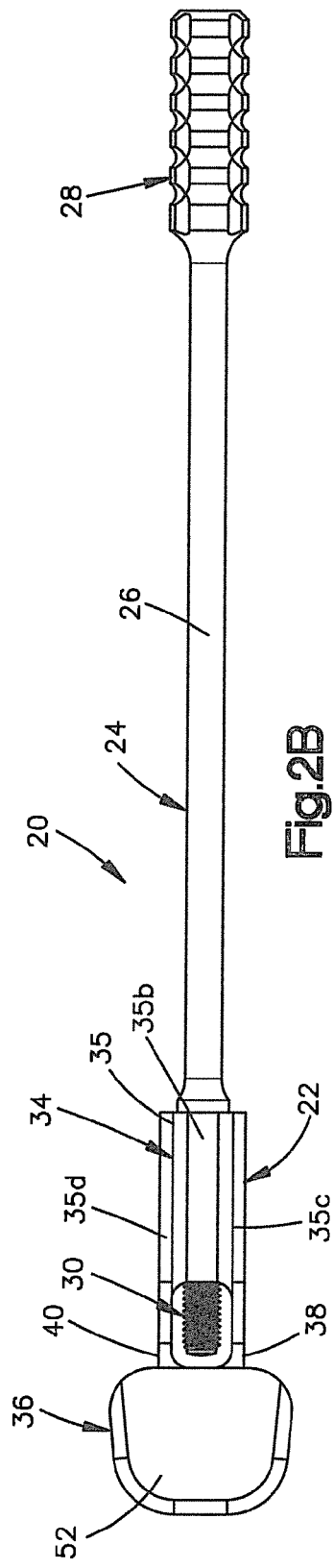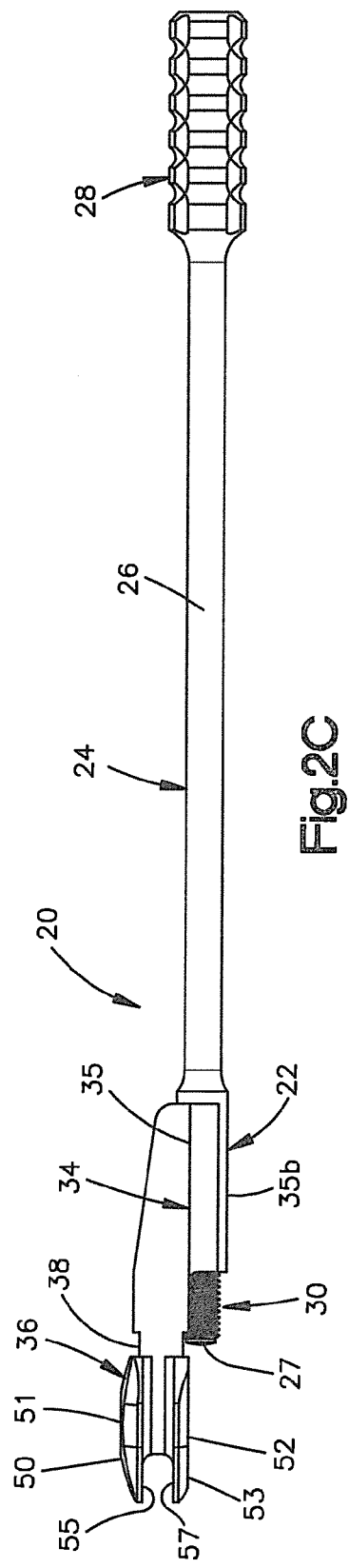

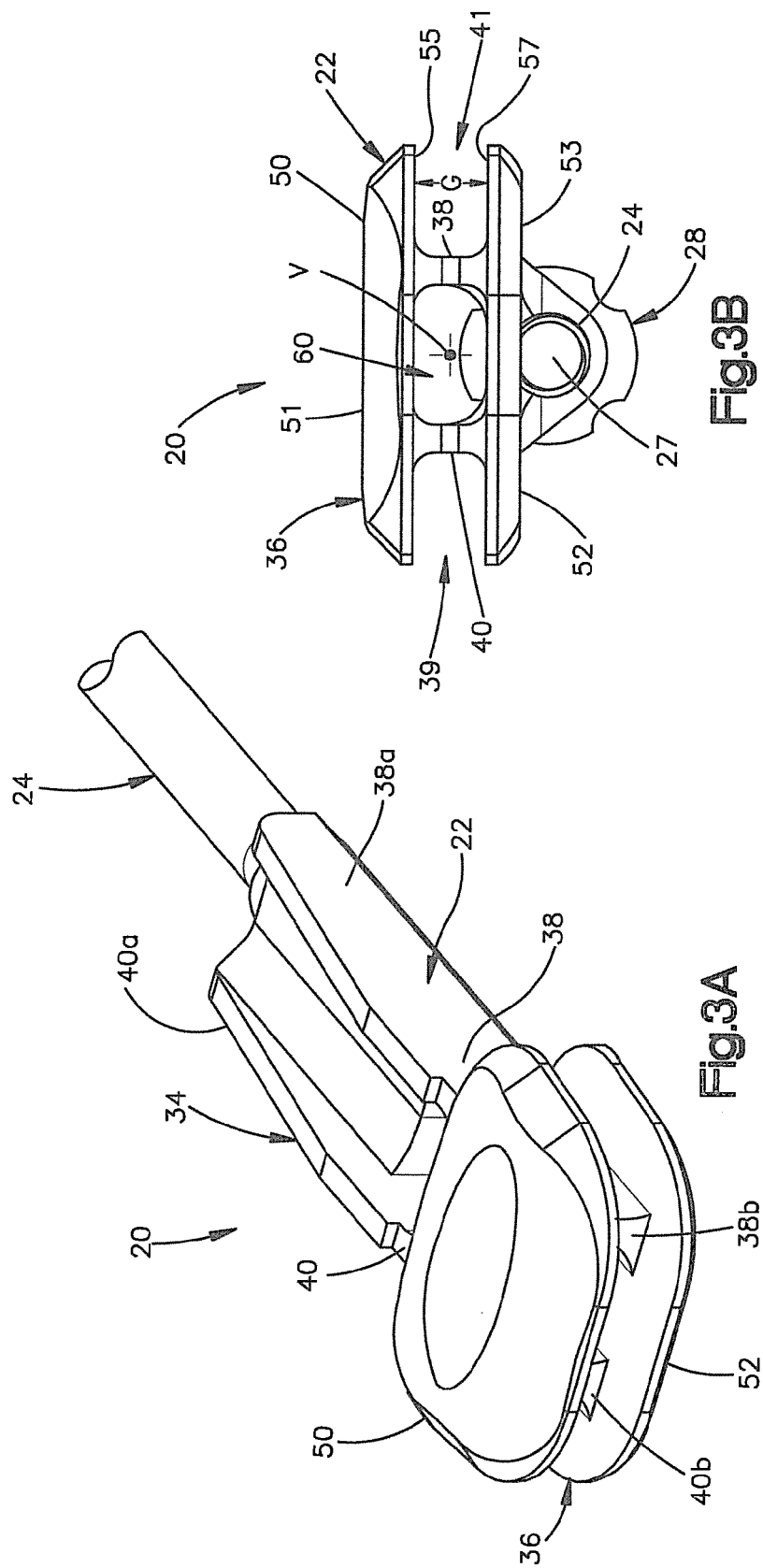

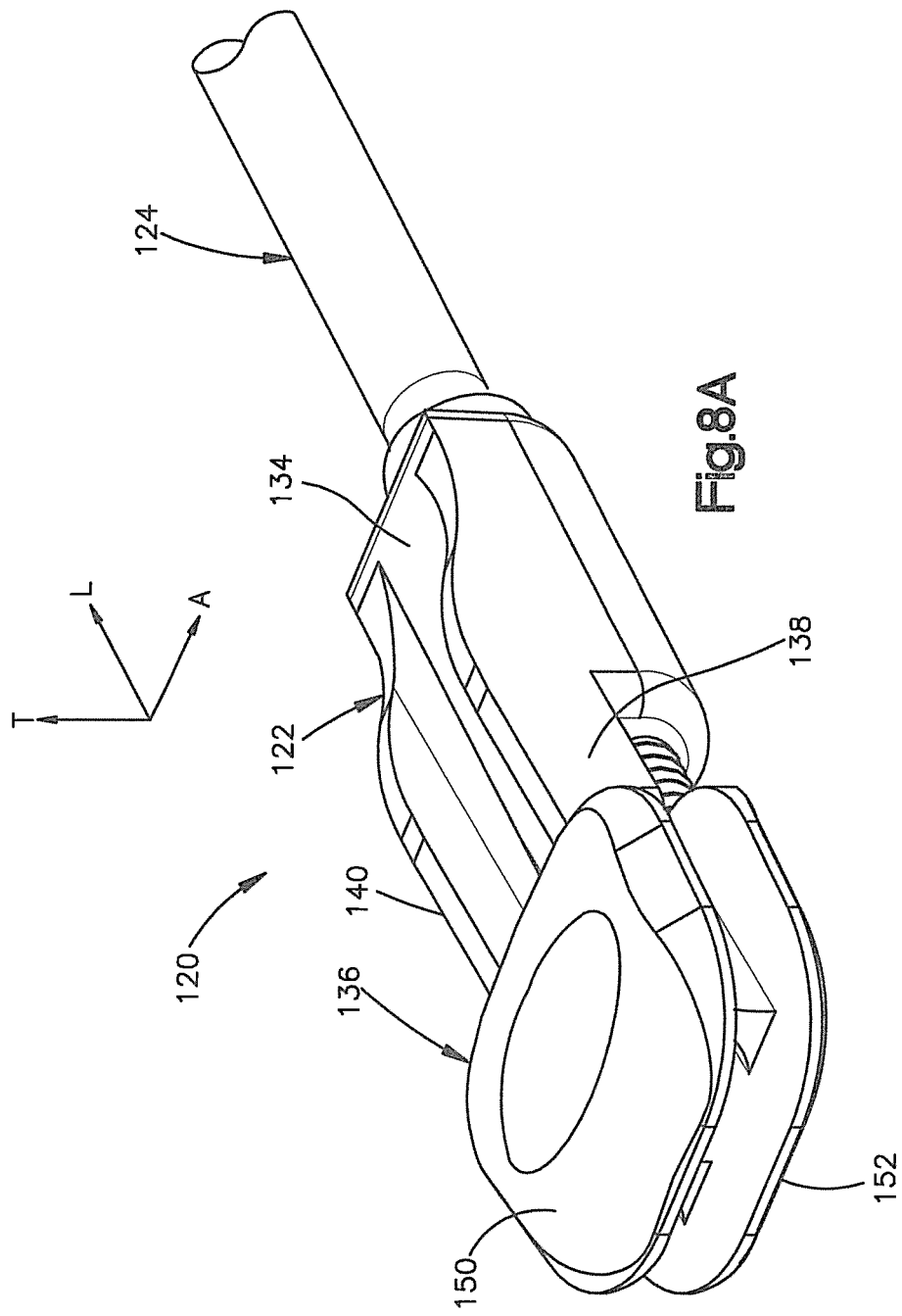

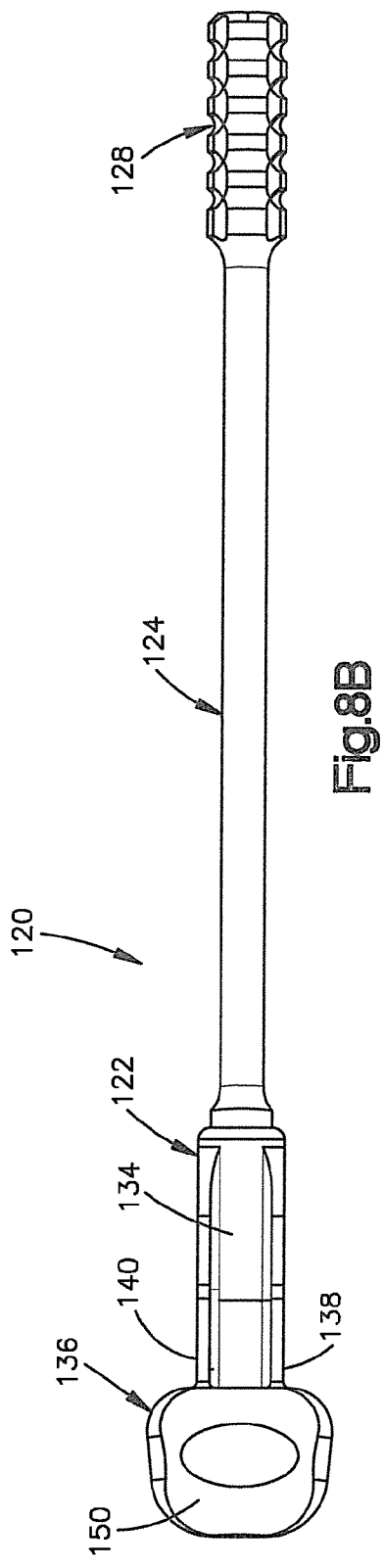
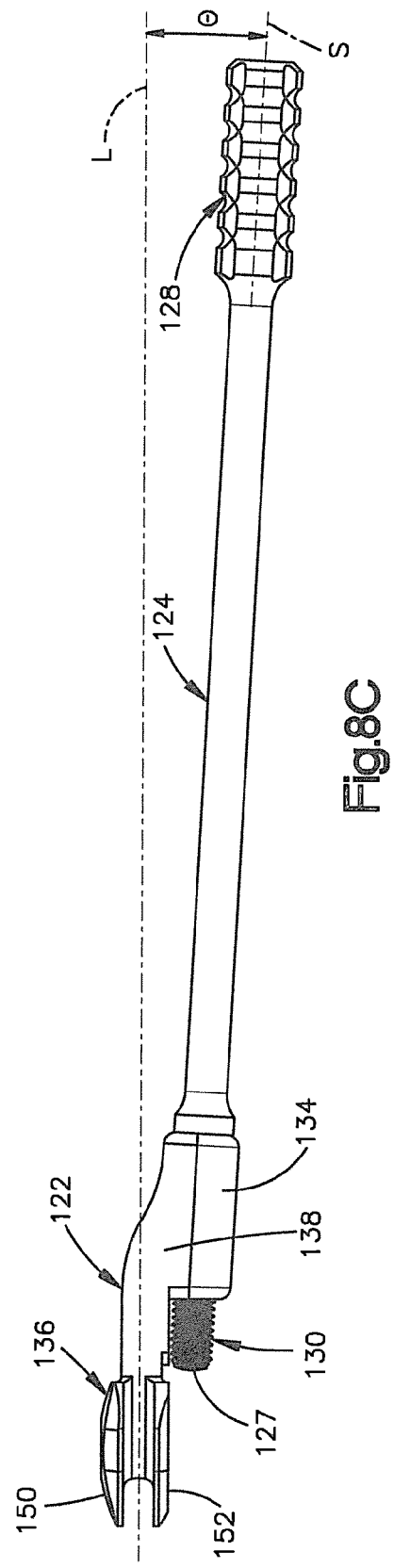
Fig.8B
Fig.8C

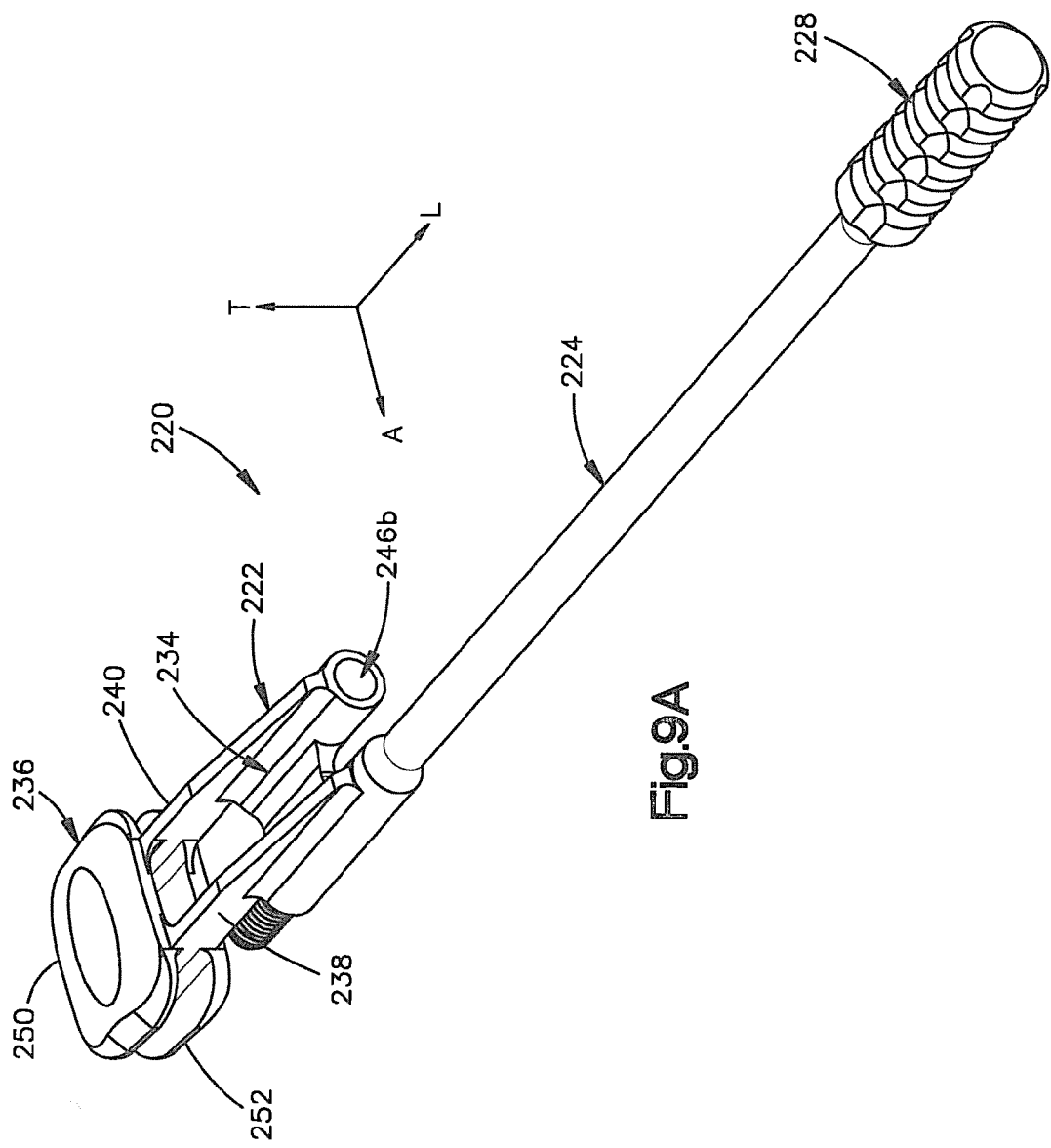

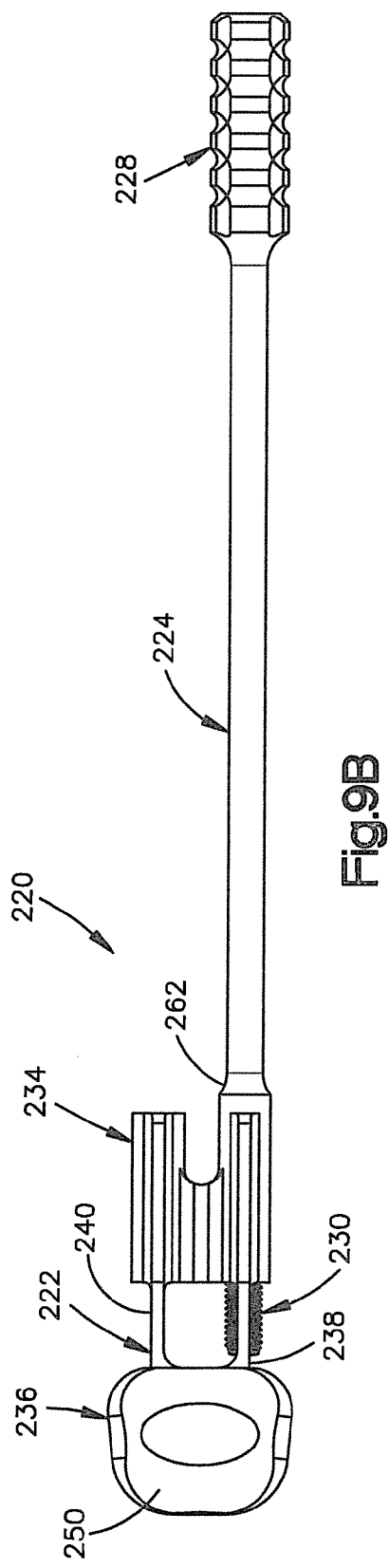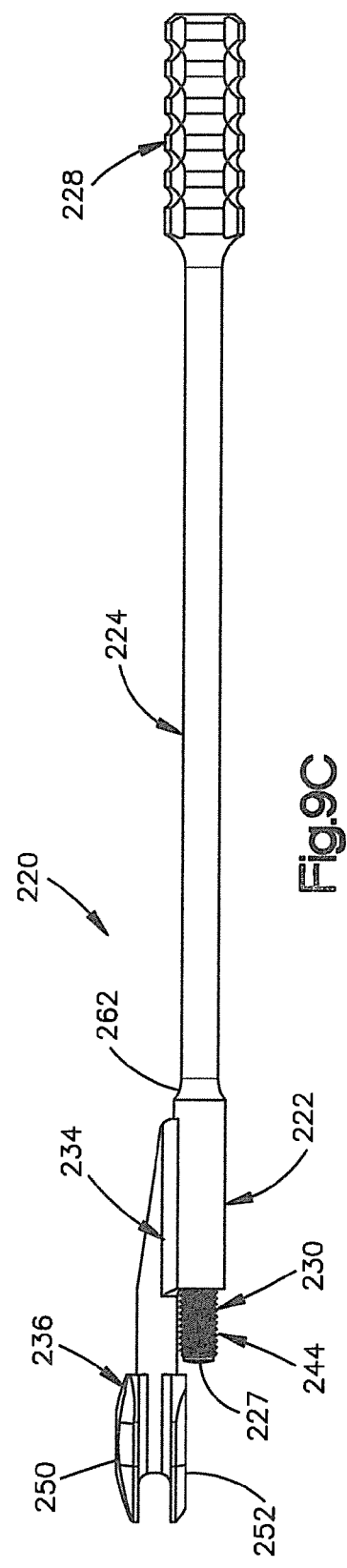

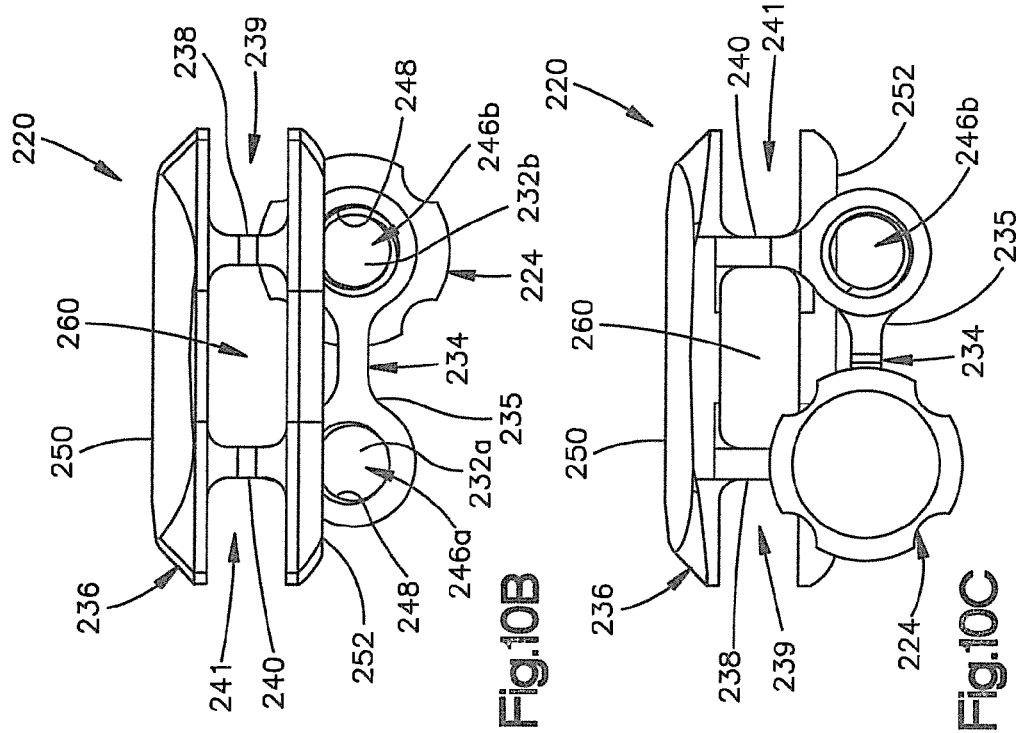
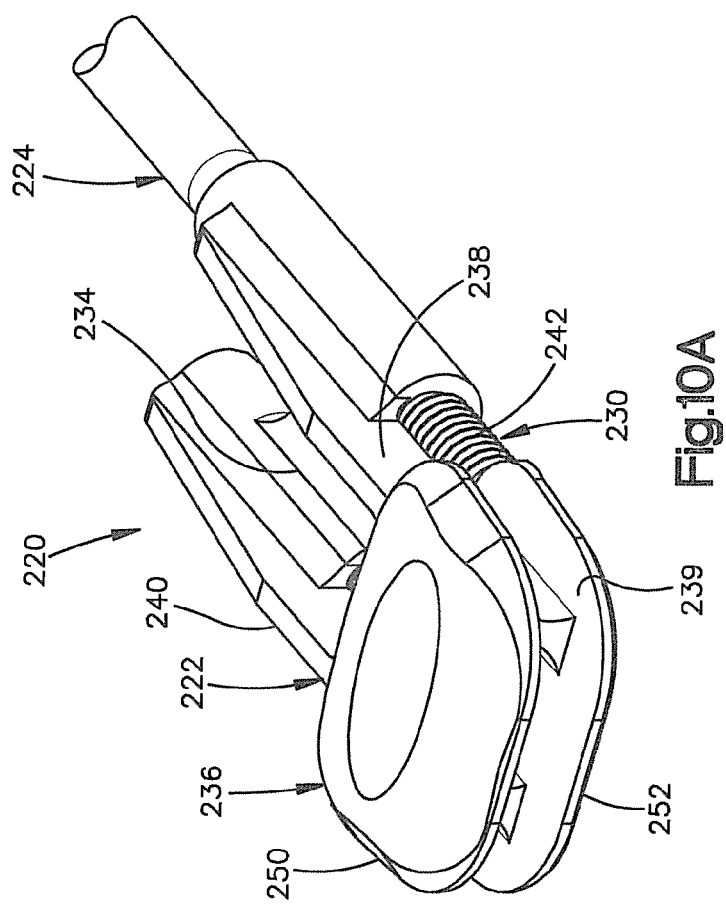

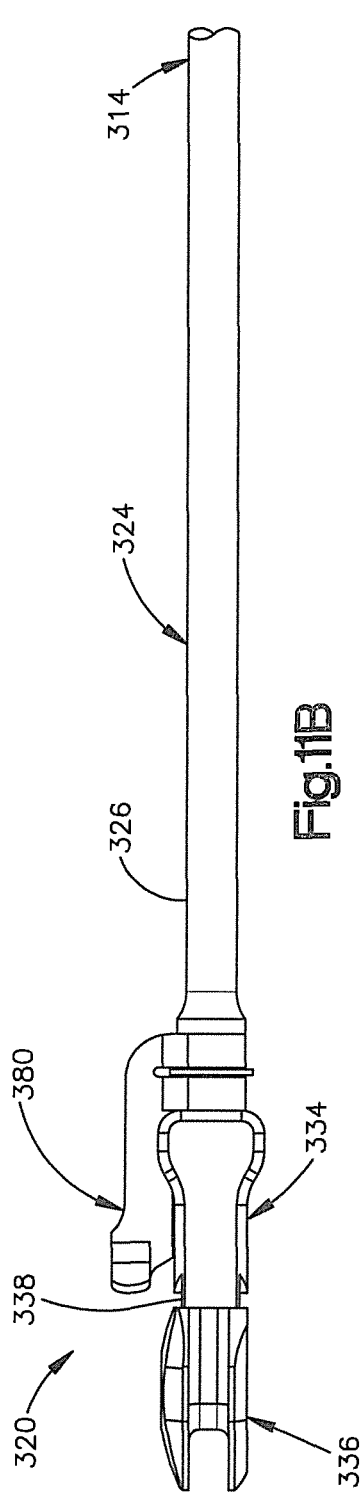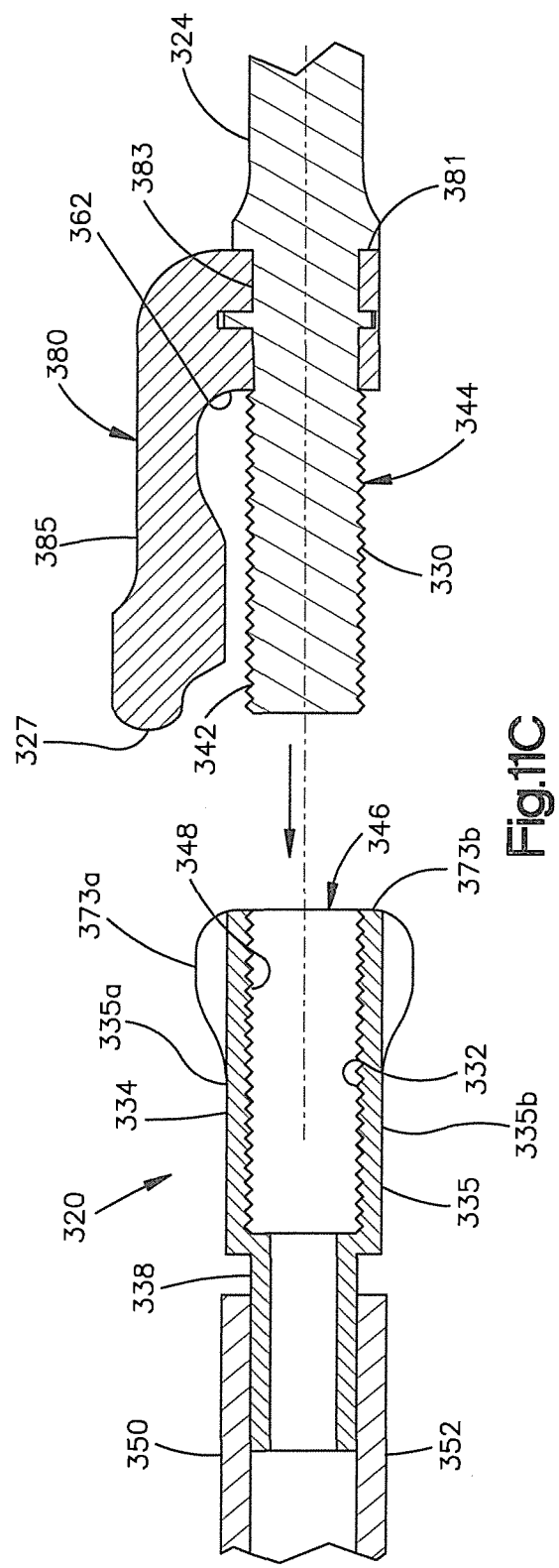

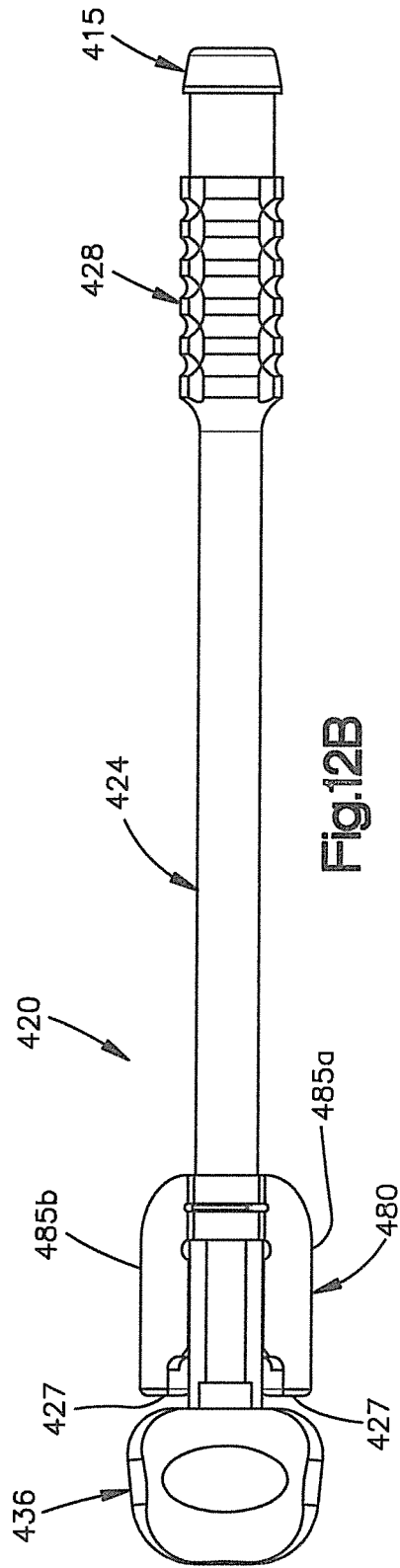
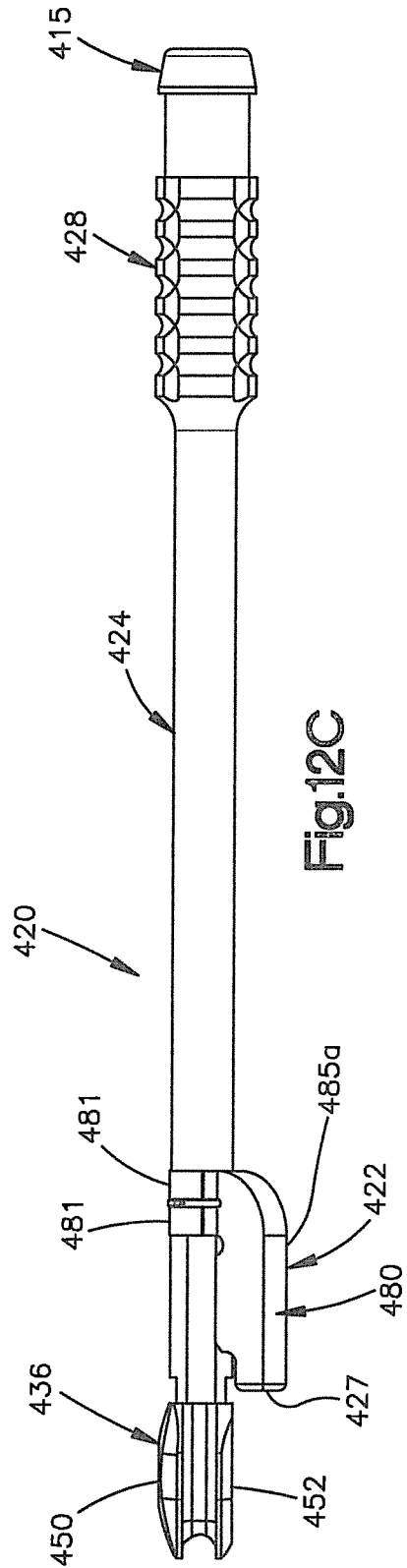

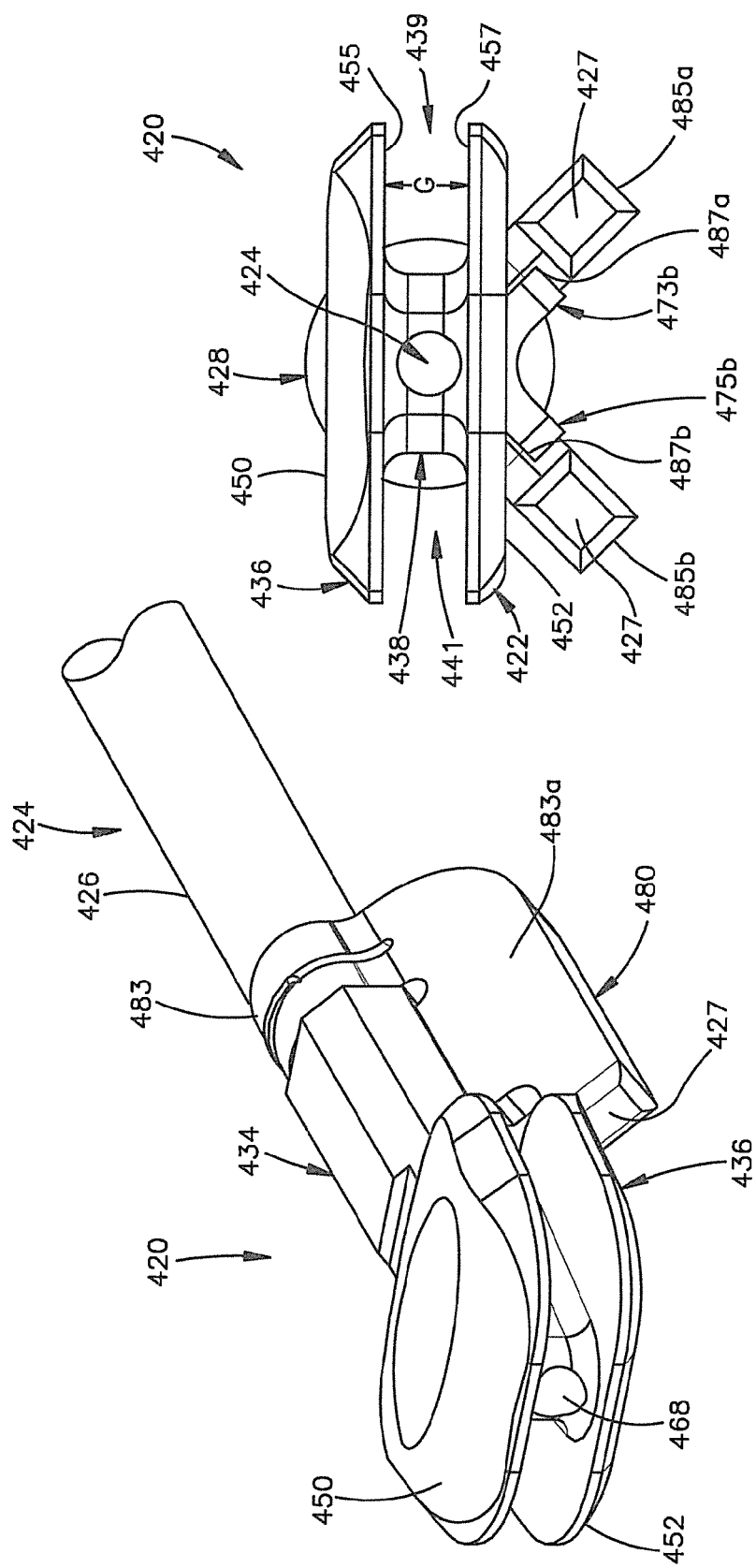

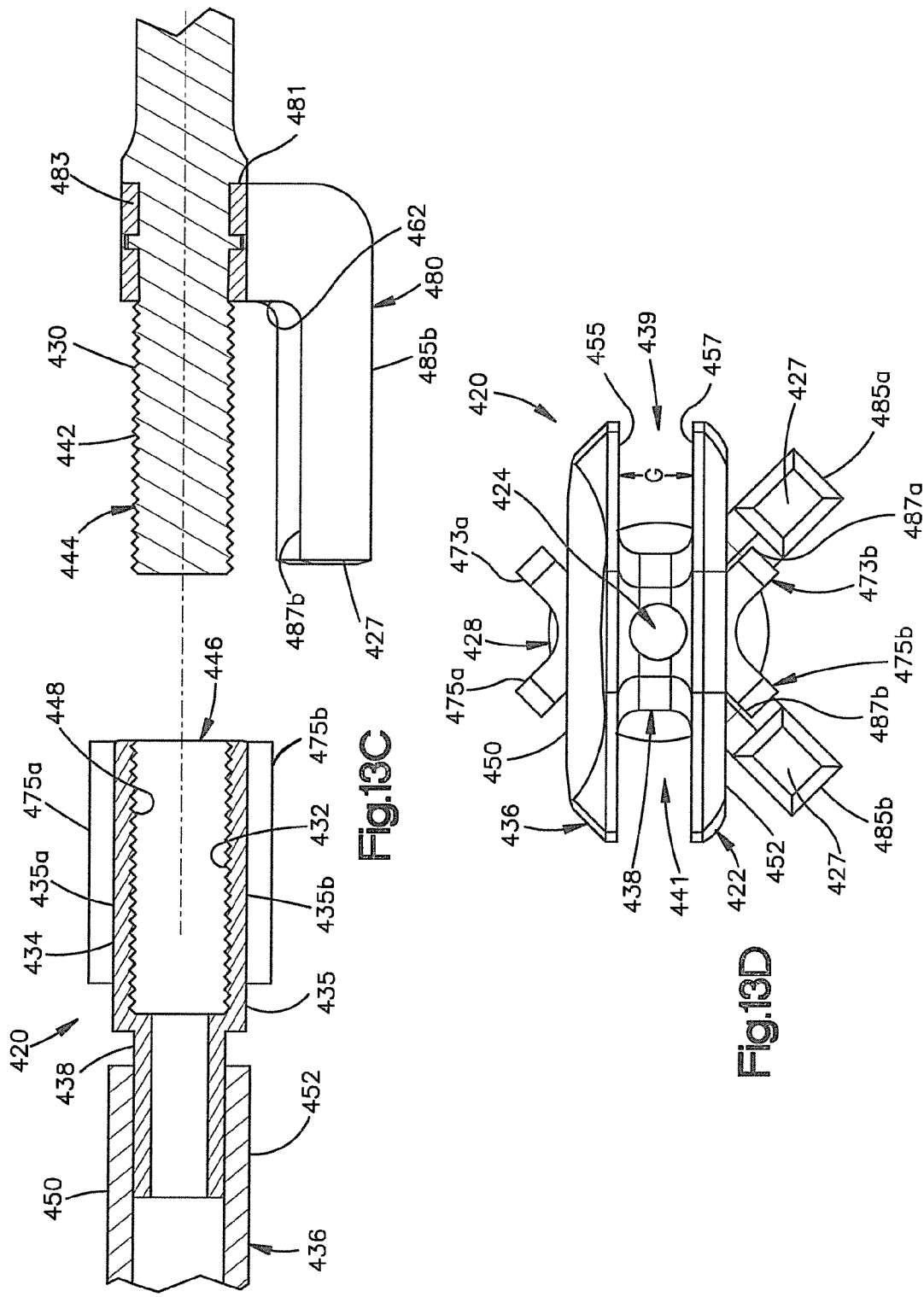

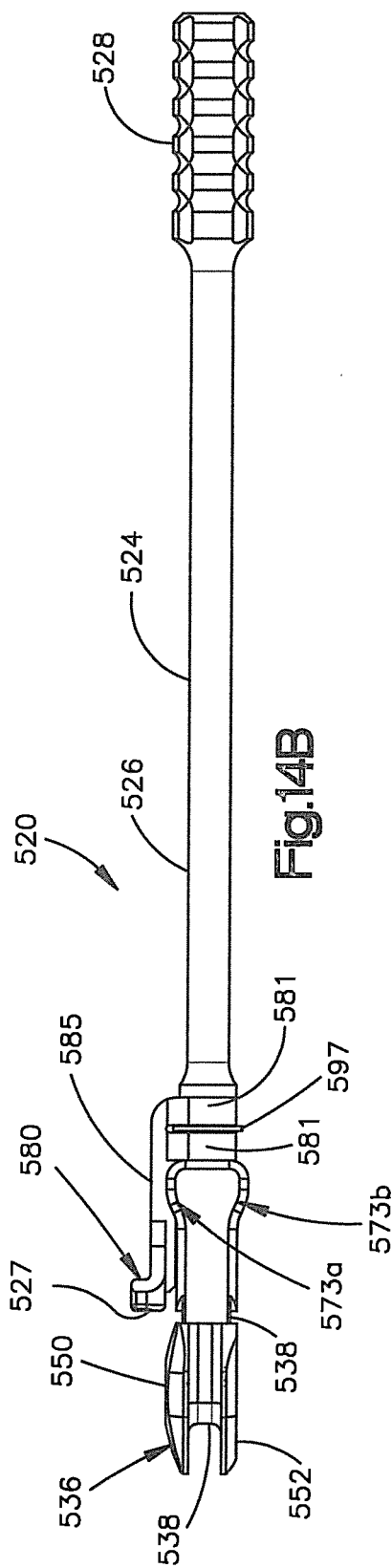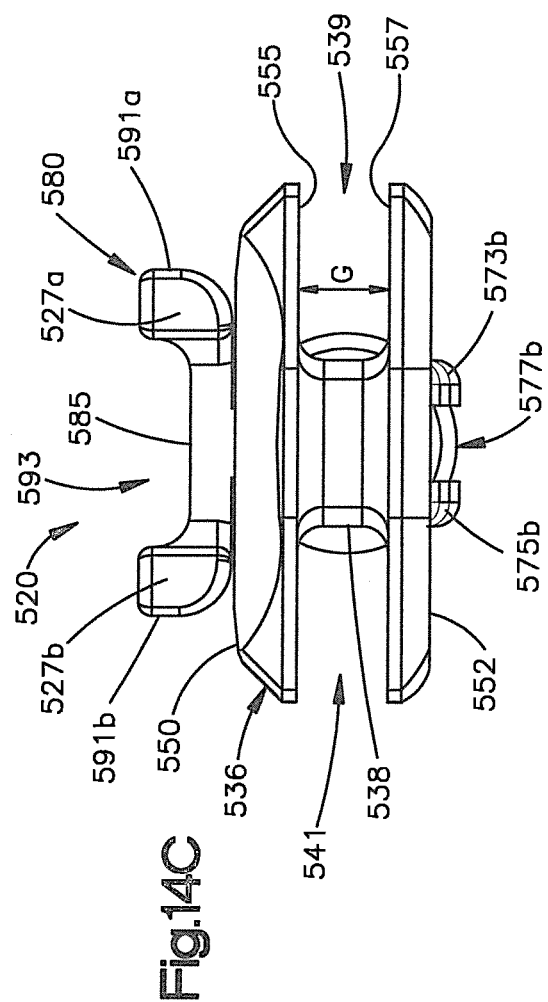

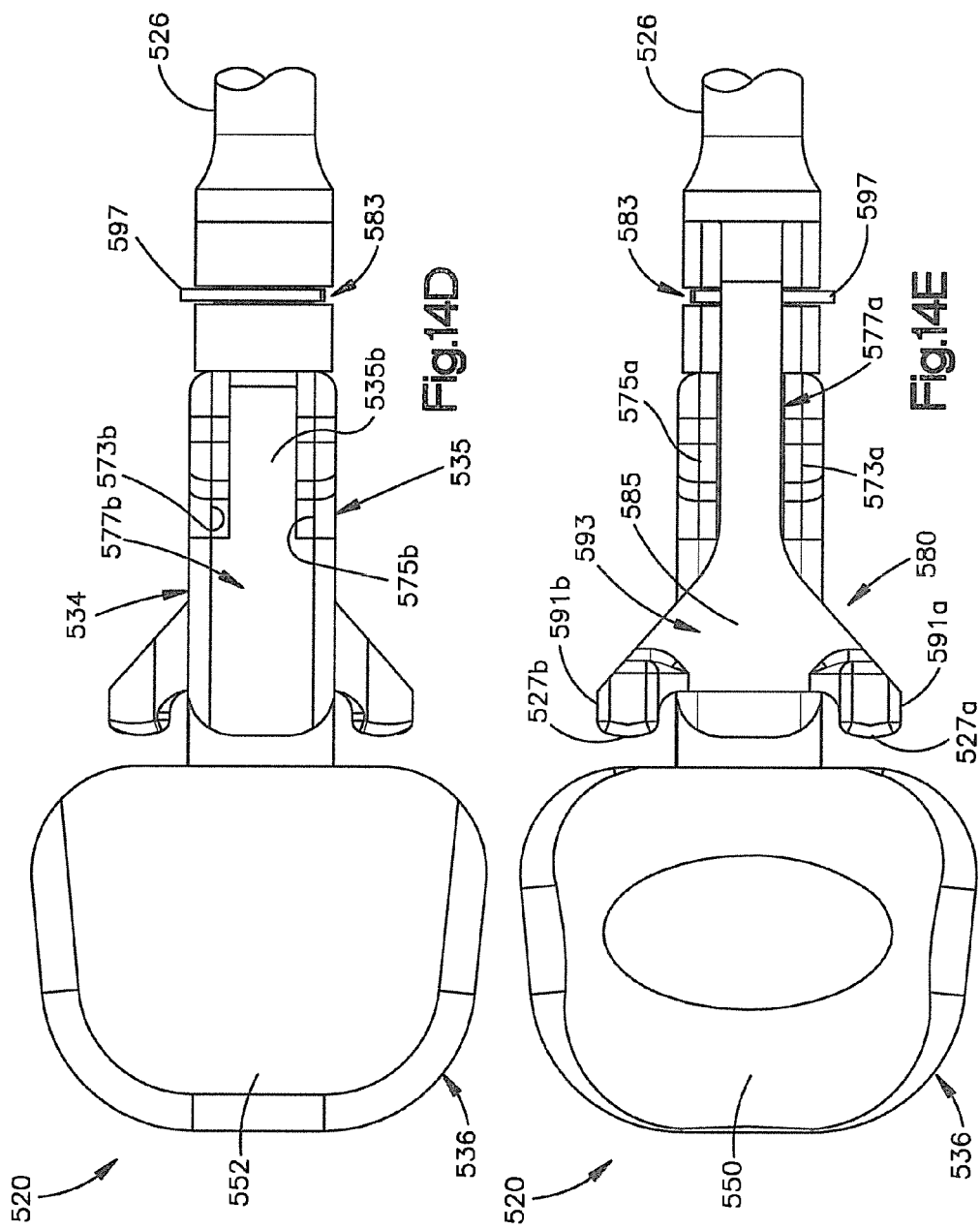

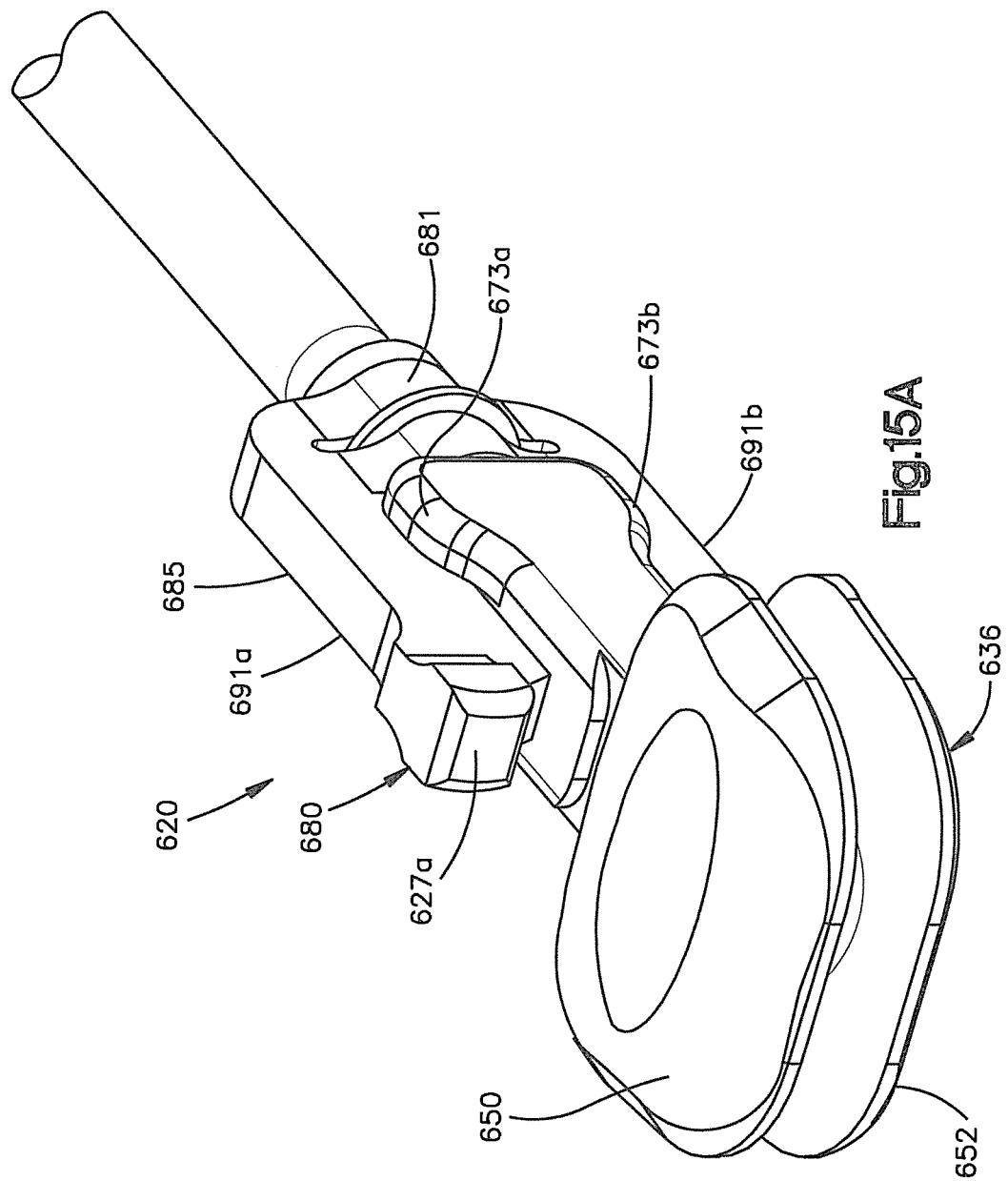

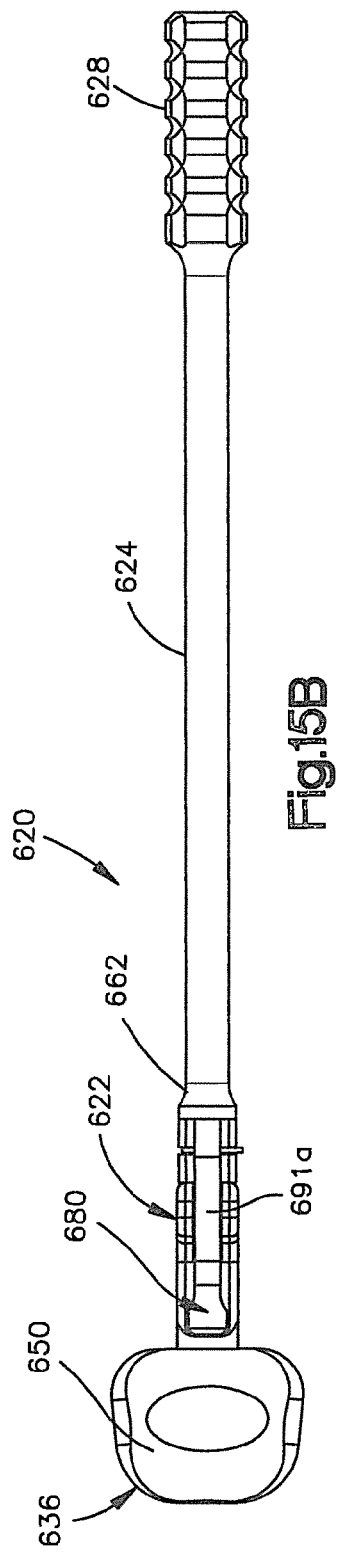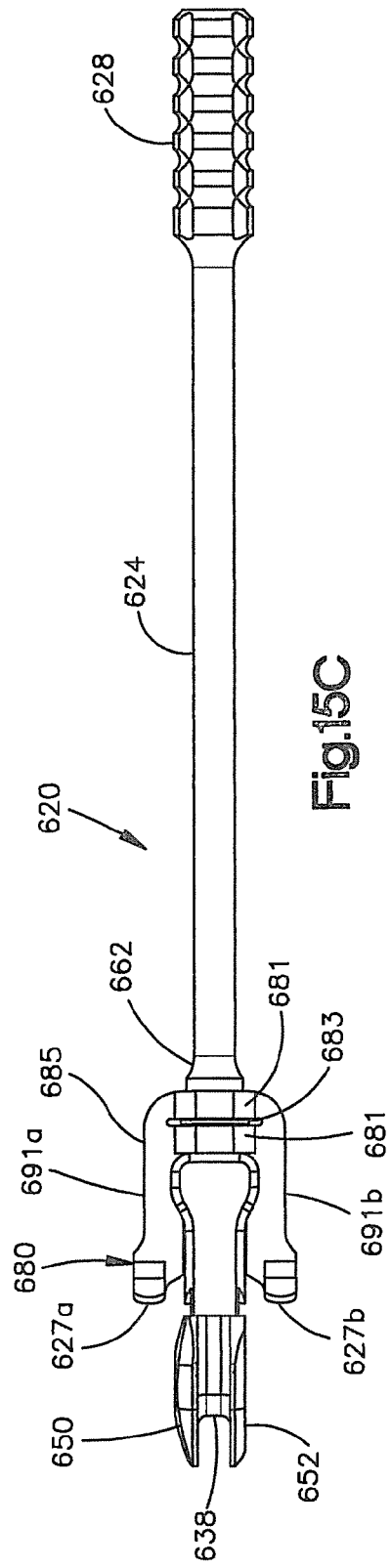

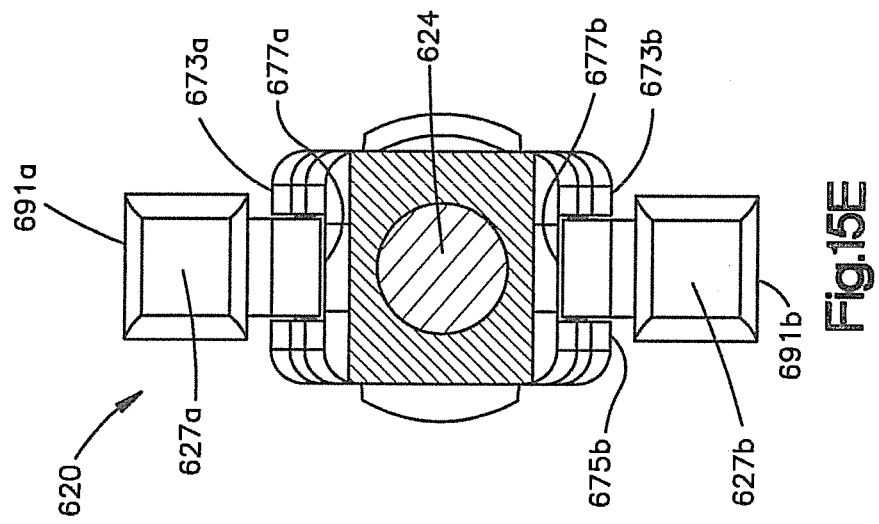
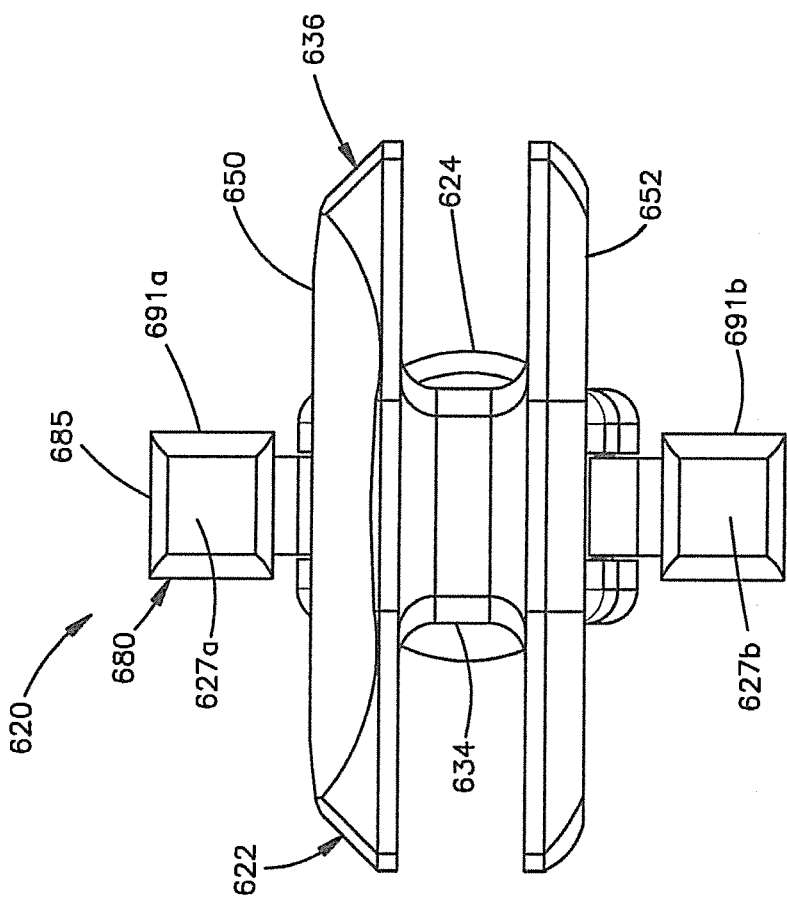
Fig.15E
Fig.15D

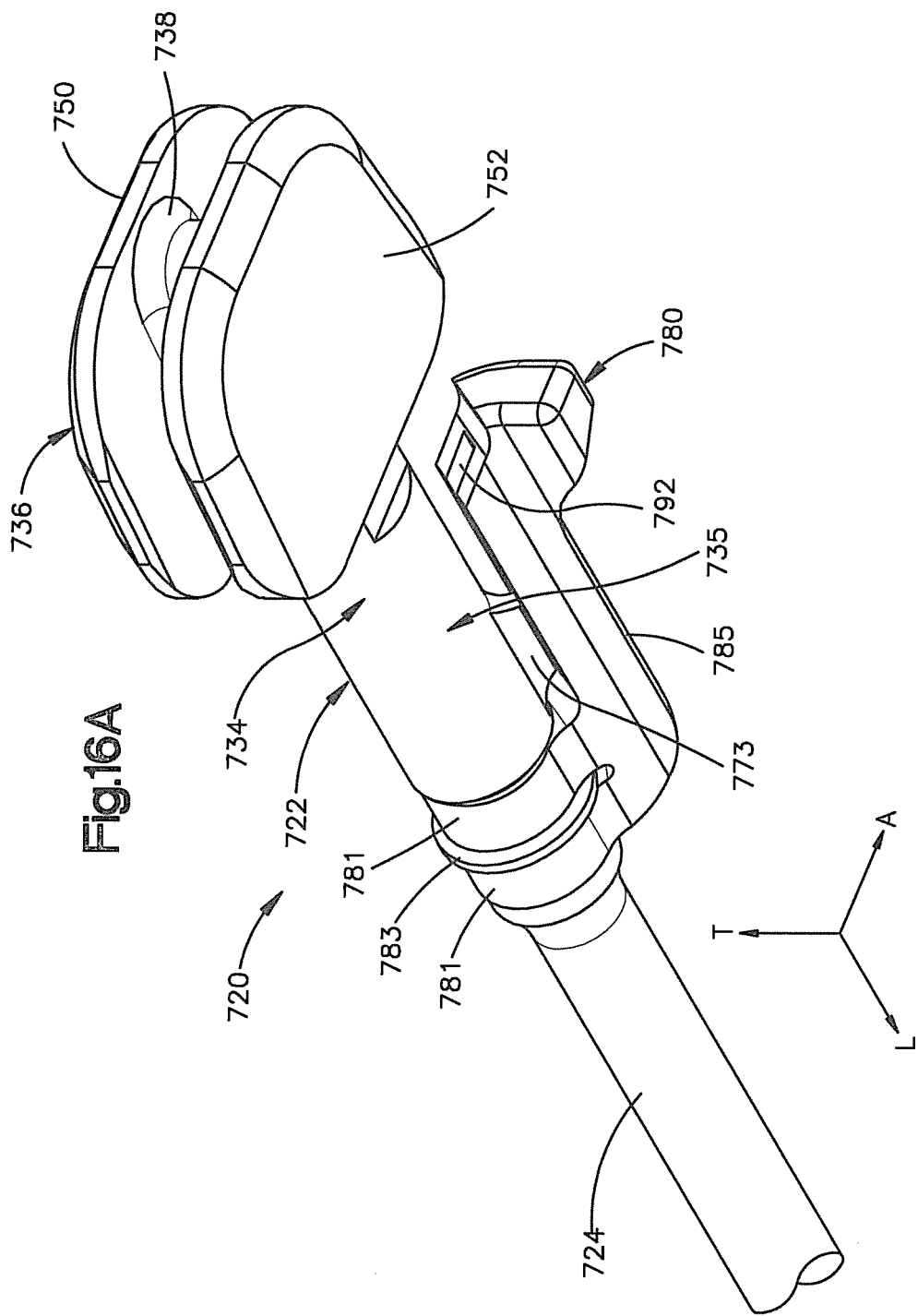

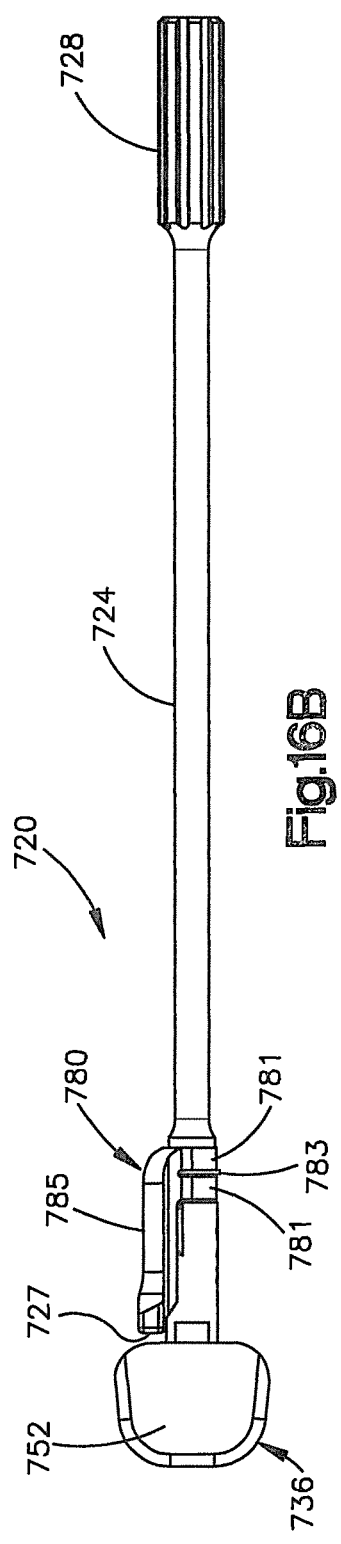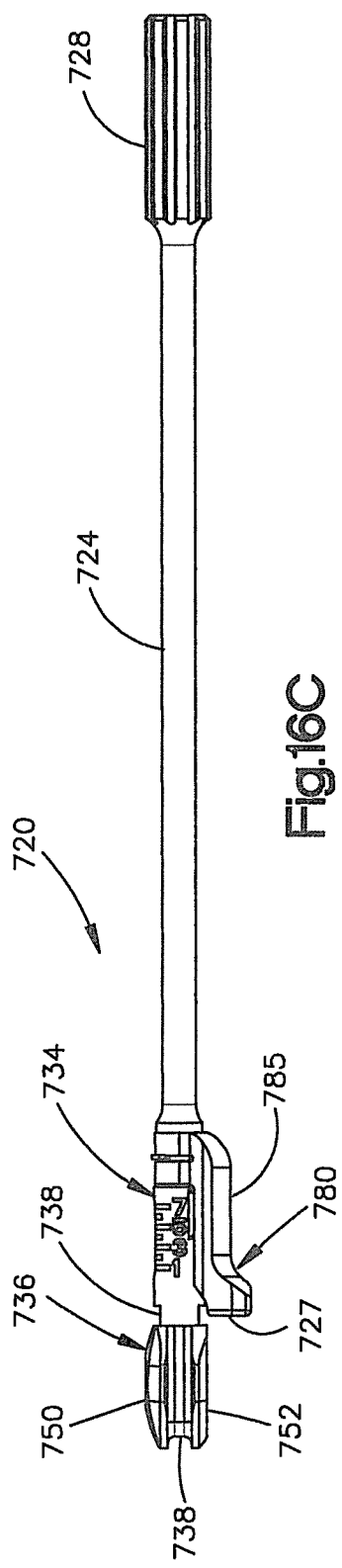

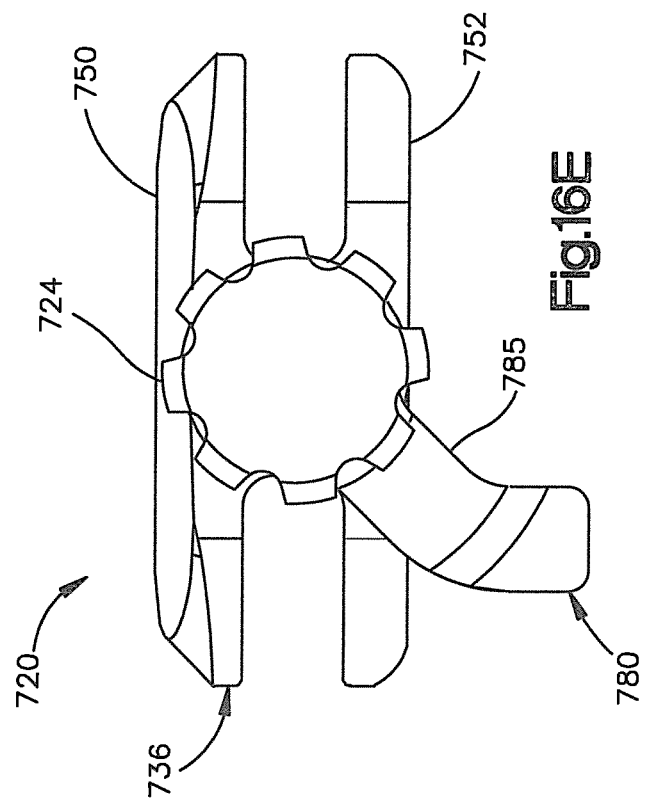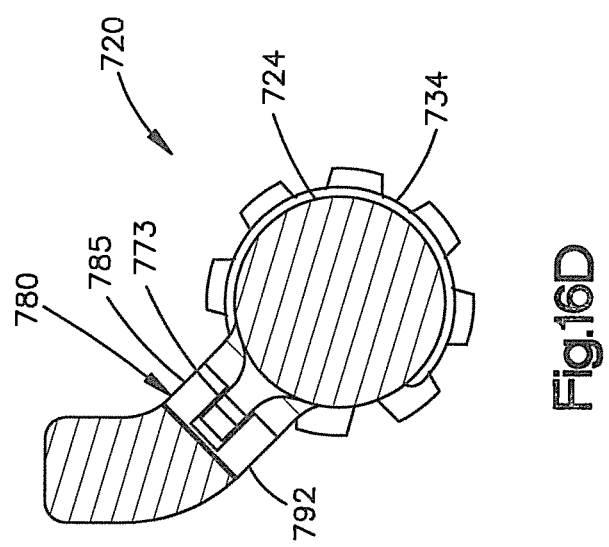

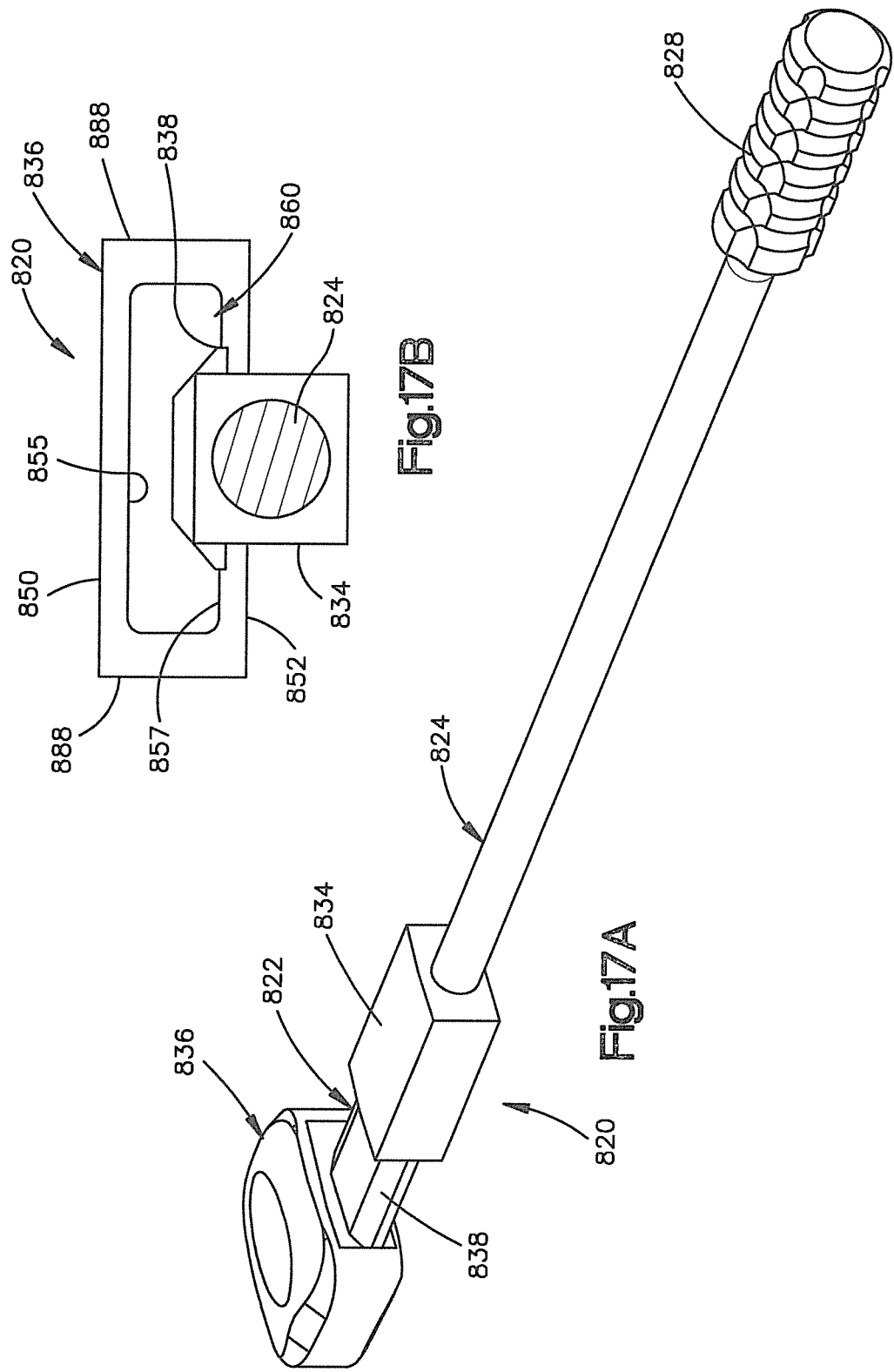

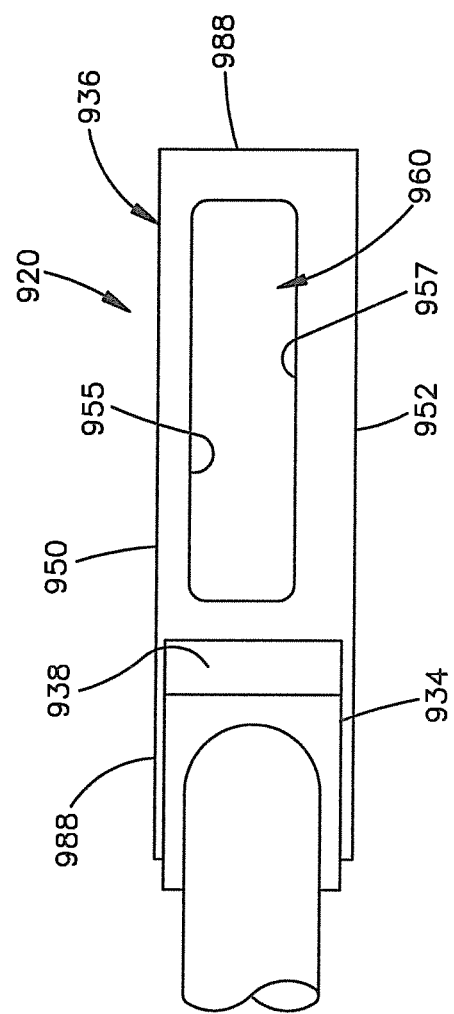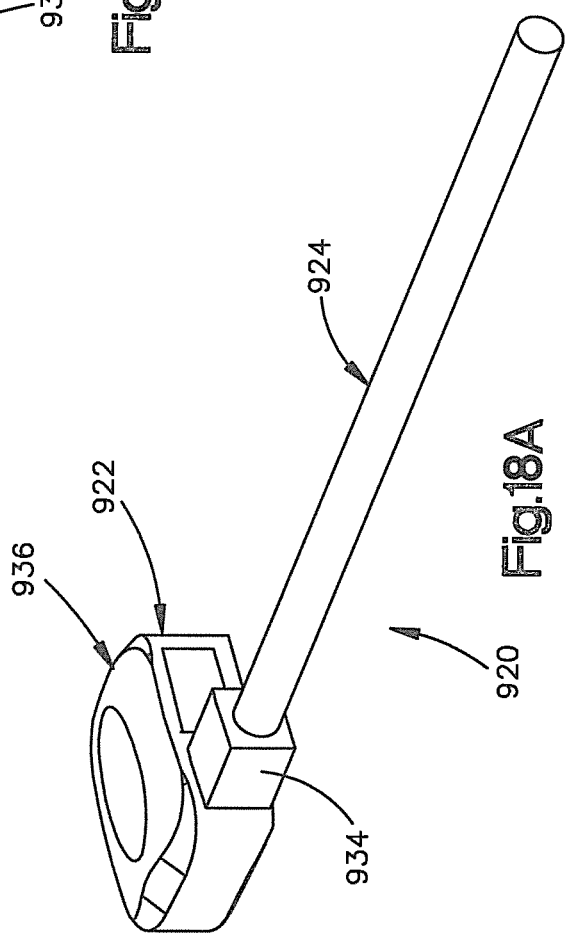
Fig.18B
Fig.18A

TRIAL IMPLANT ASSEMBLY

CROSS-REFERENCE TO RELATED APPLICATIONS

This application claims the benefit of U.S. Provisional Patent Application Ser. No. 61/169,444 filed Apr. 15, 2009, the disclosure of which is hereby incorporated by reference as if set forth in its entirety herein.

BACKGROUND

When removing a disc from an intervertebral space disposed between adjacent vertebrae, the conventional procedure is to fuse the adjacent vertebrae together. More recently, there have been developments in the field of disc replacement, namely disc arthroplasty, which involves the insertion of an artificial intervertebral disc implant into the intervertebral space. The artificial disc then allows limited universal movement of the adjacent vertebrae with respect to each other.

One such intervertebral implant includes an upper part that can communicate with an adjacent vertebrae, a lower part that can communicate with an adjacent vertebrae, and an insert located between these two parts. An example of this type of implant is disclosed in U.S. Pat. No. 5,314,477 (Marnay), the disclosure of which is hereby incorporated as if set forth in its entirety herein.

Instruments have been developed for preparing an intervertebral space for receiving an artificial disc implant. These instruments include a set of different sizes of trial implants, different ones of which are inserted into a cleaned out intervertebral space until the correct size trial implant has been determined, thereby determining the size of the actual disc implant to be permanently inserted.

In disc arthroplasty procedures, proper implant location assists in determining the kind of motion obtained from the device. Because proper implant positioning assists in patient recovery and spinal motion, fluoroscopy is used to visualize the position of the prosthesis and implant trial throughout the procedure.

BRIEF SUMMARY OF THE INVENTION

According to one aspect of the disclosure, a trial implant assembly is provided that can increase visualization of the implant and/or trial implant position while minimizing fluoroscopy, thereby reducing the amount of radiation exposure to operating room personnel and the patient.

In one embodiment, a trial implant assembly is provided that includes a trial implant configured to be inserted into an intervertebral space that is defined by a superior vertebral body and an inferior vertebral body. The trial implant includes a trial base and a trial head connected to the trial base. The trial base includes an engagement member configured to couple the trial implant to a shaft. The trial head is distally spaced from the trial base. The trial head defines a superior endplate and an inferior endplate configured to face the superior vertebral body and the inferior vertebral body, respectively. The trial head further defines at least one visualization window extending distally there-through between the superior and inferior endplates.

BRIEF DESCRIPTION OF THE SEVERAL VIEWS OF THE DRAWINGS

The foregoing summary, as well as the following detailed description of example embodiments of the invention, will be better understood when read in conjunction with the appended drawings. For the purposes of illustrating the trial implant assembly of the present application, there is shown in the drawings example embodiments. It should be understood, however, that the application is not limited to the precise arrangements and instrumentalities shown. In the drawings:

FIG. 2B is a bottom plan view of the trial implant assembly illustrated in FIG. 2A;

FIG. 2C is a side elevation view of the trial implant assembly illustrated in FIG. 2A;

FIG. 3A is a perspective view of a distal portion of the trial implant assembly illustrated in FIGS. 2A-C;

FIG. 3B is a distal end elevation view of the distal portion of the trial implant assembly illustrated in FIG. 3A;

FIG. 8A is a perspective view of a distal portion of a trial implant assembly constructed in accordance with an alternative embodiment;

FIG. 8B is a top plan view of the trial implant assembly illustrated in FIG. 8A;

FIG. 8C is a side elevation view of the trial implant assembly illustrated in FIG. 8A showing an angularly offset shaft;

FIG. 9A is a perspective view of a trial implant assembly including a shaft and a trial implant in accordance with an alternative embodiment;

FIG. 9B is a top plan view of the trial implant assembly illustrated in FIG. 9A;

FIG. 9C is a side elevation view of the trial implant assembly illustrated in FIG. 9A;

FIG. 10A is a perspective view of a distal portion of the trial implant assembly illustrated in FIGS. 9A-C;

FIG. 10B is a distal end elevation view of the distal portion of the trial implant assembly illustrated in FIG. 10A;

FIG. 10C is a proximal end elevation view of the distal portion of the trial implant assembly illustrated in FIG. 10B;

FIG. 11B is a side elevation view of the trial implant assembly illustrated in FIG. 11A;

FIG. 11C is a sectional side elevation view of the distal end of a shaft and a proximal end of a trial implant of the trial implant assembly illustrated in FIG. 11A;

FIG. 12B is a top plan view of the trial implant assembly illustrated in FIG. 12A;

FIG. 12C is a side elevation view of the trial implant assembly illustrated in FIG. 12A;

FIG. 13A is a perspective view of a distal portion of the trial implant assembly illustrated in FIGS. 12A-C;

FIG. 13B is a distal end elevation view of the distal portion of the trial implant assembly illustrated in FIGS. 12A-C;

FIG. 13C is a sectional side elevation view of the distal end of a shaft and a proximal end of a trial implant of the trial implant assembly illustrated in FIGS. 13A-B;

FIG. 13D is a distal end elevation view of the distal portion of the trial implant assembly similar to FIG. 13B, but also showing a pair of superior tracks;

FIG. 14B is a side elevation view of the trial implant assembly illustrated in FIG. 14A;

FIG. 14C is a distal end elevation view of the trial implant assembly illustrated in FIG. 14A;

FIG. 14D is a bottom plan view of a trial implant of the trial implant assembly illustrated in FIG. 14A;

FIG. 14E is a top plan view of the trial implant illustrated in FIG. 14D;

FIG. 15A is a perspective view of a distal portion of a trial implant assembly constructed in accordance with an alternative embodiment;

FIG. 15B is a top plan view of the trial implant assembly illustrated in FIG. 15A;

FIG. 15C is a side elevation view of the trial implant assembly illustrated in FIG. 15A;

FIG. 15D is a distal end elevation view of the trial implant assembly illustrated in FIG. 15A;

FIG. 15E is a sectional elevation view of the trial implant assembly illustrated in FIG. 15A;

FIG. 16A is a perspective view of a distal portion of a trial implant assembly constructed in accordance with an alternative embodiment;

FIG. 16B is a bottom plan view of the trial implant assembly illustrated in FIG. 16A;

FIG. 16C is a side elevation view of the trial implant assembly illustrated in FIG. 16A;

FIG. 16D is a sectional elevation view of a portion of the trial implant assembly illustrated in FIG. 16A;

FIG. 16E is a proximal end elevation view of the trial implant assembly illustrated in FIG. 16C;

FIG. 17A is a perspective view of a trial implant assembly constructed in accordance with an alternative embodiment;

FIG. 17B is a sectional proximal end elevation view of the trial implant assembly illustrated in FIG. 17A;

FIG. 18A is a perspective view of a trial implant assembly constructed in accordance with an alternative embodiment; and FIG. 18B is a proximal end elevation view of the trial implant assembly illustrated in FIG. 18A.

DETAILED DESCRIPTION OF THE INVENTION

Figure 1:
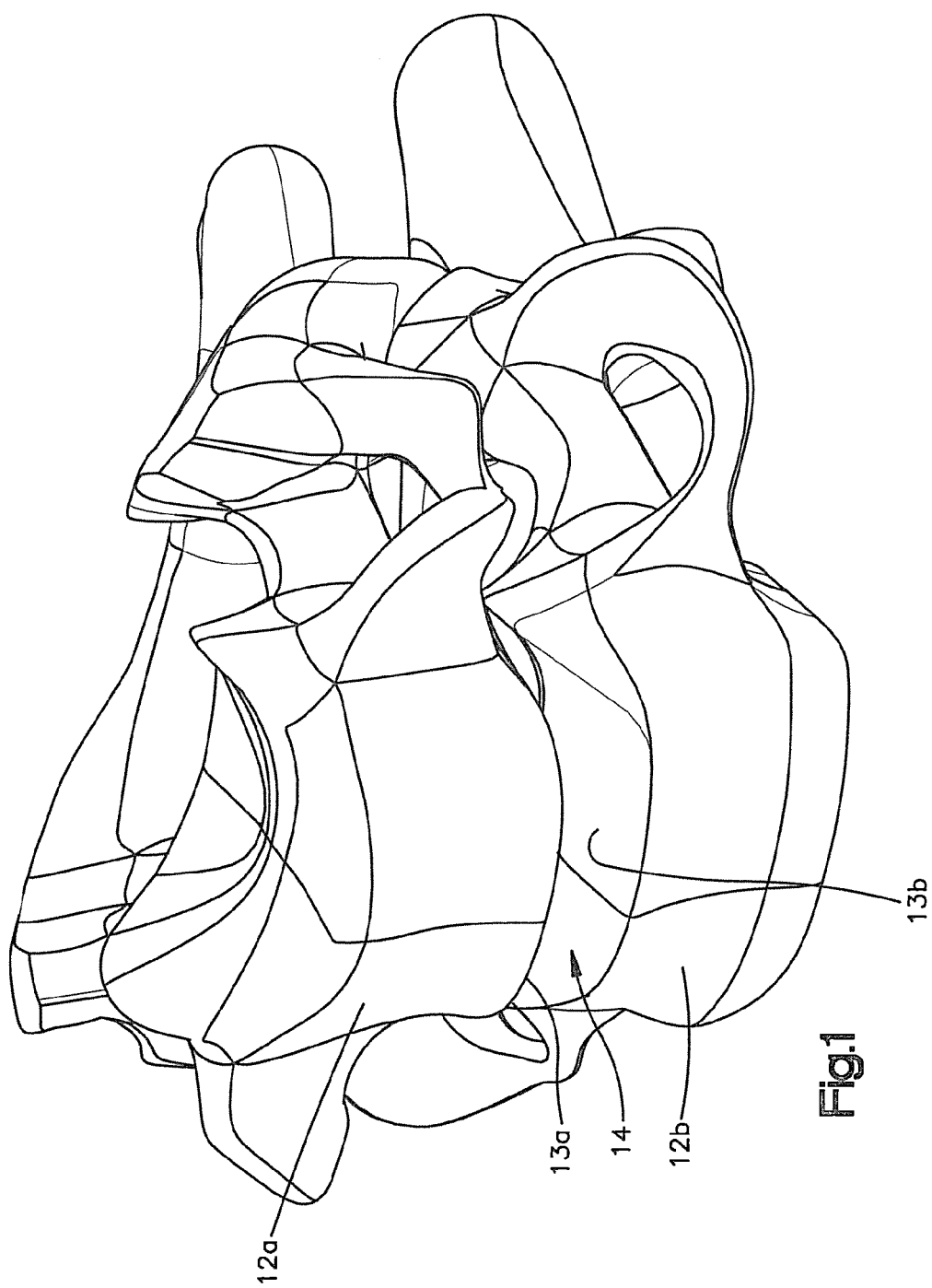
FIG. 1 is a perspective view of a pair of vertebral bodies separated by an intervertebral space.
Figure 2A:
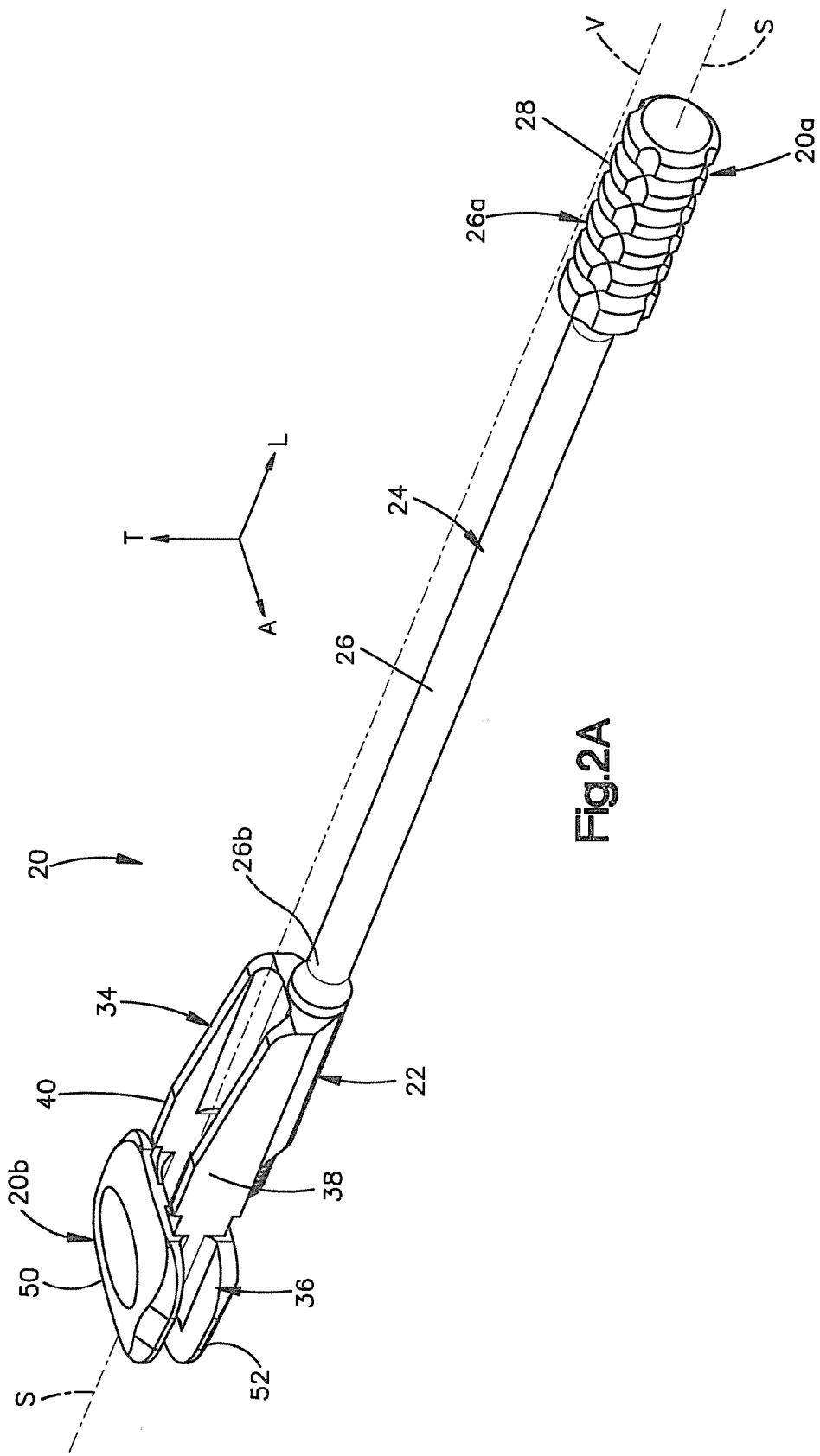
FIG. 2A is a perspective view of a trial implant assembly including a shaft and a trial implant in accordance with one embodiment.

Referring to FIG. 1, a superior vertebral body 12a defines a superior vertebral surface 13a of an intervertebral space 14, and an adjacent inferior vertebral body 12b defines an inferior vertebral surface 13b of the intervertebral space 14. Thus, the intervertebral space 14 is disposed between the vertebral bodies 12a-b. The vertebral bodies 12a-b can be anatomically adjacent vertebral bodies, or can remain after a discectomy has been performed that removed a vertebral body from a location between the vertebral bodies 12a-b. As illustrated, the intervertebral space 14 is illustrated after a discectomy, whereby the disc material has been removed or at least partially removed to prepare the intervertebral space 14 to receive a disc implant that can achieve height restoration. Prior to inserting the permanent disc implant in the intervertebral space, one or more trial implants of various sizes, such as the trial implant 22 of a trial implant assembly 20 illustrated in FIG. 2, are inserted into the intervertebral space 14 until the correctly sized trial implant has been determined, thereby determining the size of the actual disc implant to be permanently inserted. The intervertebral space 14 can be disposed anywhere along the spine as desired.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

The trial implant assembly 20 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the trial implant 20 is implanted into an intervertebral space, such as the intervertebral space 14, the transverse direction T extends generally along the superior-inferior (or caudal-cranial) direction, while the plane defined by the longitudinal direction L and lateral direction A lie generally in the anatomical plane defined by the anterior-posterior direction, and the medial-lateral direction. Accordingly, the directional terms "vertical" and "horizontal" are used to describe the implant assembly 20 and its components as illustrated merely for the purposes of clarity and illustration.

Referring now also to FIGS. 2A-2D, a trial implant assembly 20 is configured to be positioned within an at least a partially cleared out disc space, such as the disc space 14 disposed between the superior vertebral body 12a and the inferior vertebral body 12b. The trial implant assembly 20 includes a trial implant 22 coupled to a shaft 24. The shaft 24 can be formed from any desired material such as stainless steel, while the trial implant 22 can be formed from any desired material such as a titanium alloy. It should be appreciated that both the shaft 24 and the trial implant 22 can be formed from a range of biocompatible metals or polymers, such as cobalt chromium molybdenum (CoCrMo), titanium and titanium alloys, stainless steel, ceramics, or polymers such as polyetheretherketone (PEEK), polyetherketoneketone (PEKK), and bioresorbable materials.

The shaft 24 includes a shaft body 26 that defines a proximal end 26a, and a distal end 26b that is separated from the proximal end 26a along a longitudinally extending central shaft axis S. The shaft 24 includes a handle 28 or gripping portion at the proximal end 26a of the shaft body 26, and a trial implant engagement member 30 at the distal end 26b of the shaft body 26. The handle 28 can be knurled or otherwise textured to facilitate an ergonomically friendly gripping surface. The shaft body 26 defines, and thus carries, a vertebral abutment surface 27 at the distal end 26b. The engagement member 30 is configured to be coupled to a complementary engagement member 32 of the trial implant 22 so as to connect the shaft 24 to the trial implant 22.

Thus, the proximal end 26a of the shaft body 26 defines a proximal end 20a of the implant assembly 20, and the trial implant 22 defines an opposed distal end 20b of the implant assembly 20. Accordingly, a distal spatial relationship is used herein to refer to a longitudinal direction from the proximal end 20a toward the distal end 20b, and a proximal spatial relationship is used herein to refer to a longitudinal direction from the distal end 20b toward the proximal end 20a.

Figure 2D:
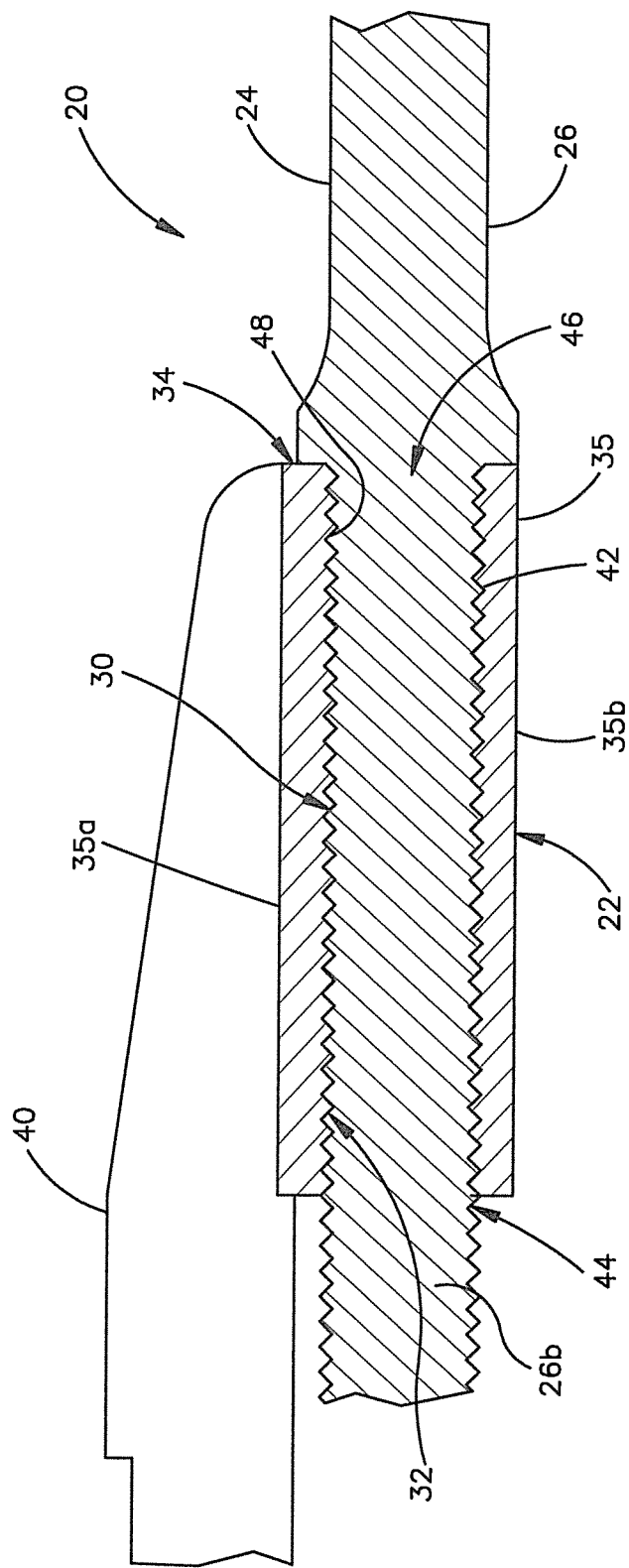
FIG. 2D is a sectional side elevation view of a portion of the trial implant assembly illustrated in FIG. 2A.

The trial implant 22 generally includes a trial base 34 coupled to the shaft 24, a trial head 36 that is disposed distally from the trial base 34, and a pair of laterally spaced ribs 38 and 40 that are fixedly connected between the trial head 36 and the trial base 34. Thus, the trial base 34 is connected indirectly to the trial head 36 via the ribs 38 and 40, though it should be appreciated that the trial base 34 could alternatively be directly connected to the trial head 36. The trial base 34 includes a trial base body 35 having transversely opposed upper and lower surfaces 35a and 35b, and laterally opposed outer surfaces 35c and 35d. As illustrated in FIG. 2D, the trial base 34 defines an engagement member 32 that is configured to connect to the engagement member 30 of the shaft 24.

In particular, the engagement member 30 of the shaft 24 is illustrated as including external threads 42 disposed in a threaded region 44 proximate to the distal end 26b of the shaft 26. The trial implant 22 includes an aperture 46 that extends longitudinally through the trial base body 35. The aperture 46 is sized to receive the threaded region 44 of the shaft 24. The engagement member 32 of the trial base 34 includes internal threads 48 disposed about the periphery of the aperture 46 that are configured to mate with the external threads 42 of the shaft 24 so as to couple the shaft 24 to the trial implant 22.

Referring now to FIGS. 2A-3B, the trial head 36 includes an upper or superior endplate 50 that defines an upper or superior, or outer transverse, engagement surface 51 configured to contact the inferior endplate 13a of the superior vertebral body 12a, and an inferior endplate 52 that defines a lower or inferior, or outer transverse, engagement surface 53 configured to contact the superior endplate 13b of the inferior vertebral body 12b. The superior endplate 50 further defines a lower or inferior, or inner transverse, surface 55, and the inferior endplate 52 defines an upper or superior, or inner transverse, surface 57. The surfaces 55 and 57 are spaced vertically along the transverse direction T by a gap G as illustrated, though it should be appreciated that the endplates 50 and 52 could alternatively be connected at their inner transverse ends. Thus, reference to superior endplates and inferior endplates is not intended to be limited to a pair of spaced apart endplates unless otherwise indicated.

As described above, the trial implant assembly 20 includes a pair of ribs 38 and 40 that are connected between the trial base 34 and the endplates 50 and 52, such that the ribs 38 and 40 define side walls of the trial head 36. Some or all of endplates 50 and 52, the trial base 34, and the ribs 38 and 40 can be integrally connected or discretely connected as desired. The ribs 38 and 40 define respective proximal ends 38a and 40a that are connected to the opposed lateral sides 35c and 35d of the trial base 34, and respective distal ends 38b and 40b that are connected to the endplates 50 and 52.

The distal ends 38b and 40b are connected between the inner transverse surfaces 55 and 57, and are laterally spaced apart so as to at least partially define an aperture or visualization window 60 that extends longitudinally through the trial head 36. The visualization window 60 is defined between the inner transverse surfaces 55 and 57 of the superior and inferior endplates 50 and 52, respectively, and the ribs 38 and 40. Thus, the visualization window 60 is enclosed, and extends transversely between the inner transverse surfaces 55 and 57, and laterally between the ribs 38 and 40. The trial head 36 further defines first and second laterally opposed slots 39 and 41 that are disposed on opposite sides of the window 60, and are separated from the window by the first and second ribs 38 and 40, respectively. The slots 39 and 41 are thus closed on their laterally inner ends, but open at their laterally outer ends. Accordingly, the slots 39 and 41 can be referred to as being open. The distal ends of the first and second ribs 38 and 40 terminate proximal to the distal end of the trial head 36, or endplates 50 and 52, so as to provide increased visualization and allow improved access to posterior structures in the disc space using a conventional nerve hook or probe.

In this regard, it should be appreciated that the trial implant assembly 22 is devoid of structure that obstructs a straight visualization axis V from extending from a first location disposed proximal to the handle 28 to a second location that passes through the visualization window 60. Otherwise stated, the trial implant defines a visualization window such as window 60, at least a portion of which up to all of which is visually unobstructed. The visualization axis V can extend parallel to the central shaft axis S as illustrated, or can extend at an angle with respect to the central shaft axis S.

The distal ends 38b and 40b vertically offset with respect to the proximal ends 38a and 40a of the ribs 38 and 40, such that the gap G between the endplates 50 and 52 is at least partially vertically offset with respect to the aperture 46 and the shaft 24, as well as the upper surface 35a of the trial base 34. In accordance with the illustrated embodiment, the distal ends 38b and 40b are disposed above the proximal ends 38a and 40a of the ribs 38 and 40, such that the gap G between the endplates 50 and 52 is disposed at least partially above the aperture and shaft 24, as well as the upper surface 35a of the trial base 34. In this regard, it should be appreciated that the inner transverse surface 57 of the inferior endplate 52 can be disposed above or below the upper surface 35a of the trial base 34. Accordingly, visualization is possible through the visualization window 60 along a distal direction from a location proximal of the trial head 36, and further from a location proximal of the handle 28.

Figure 4A:
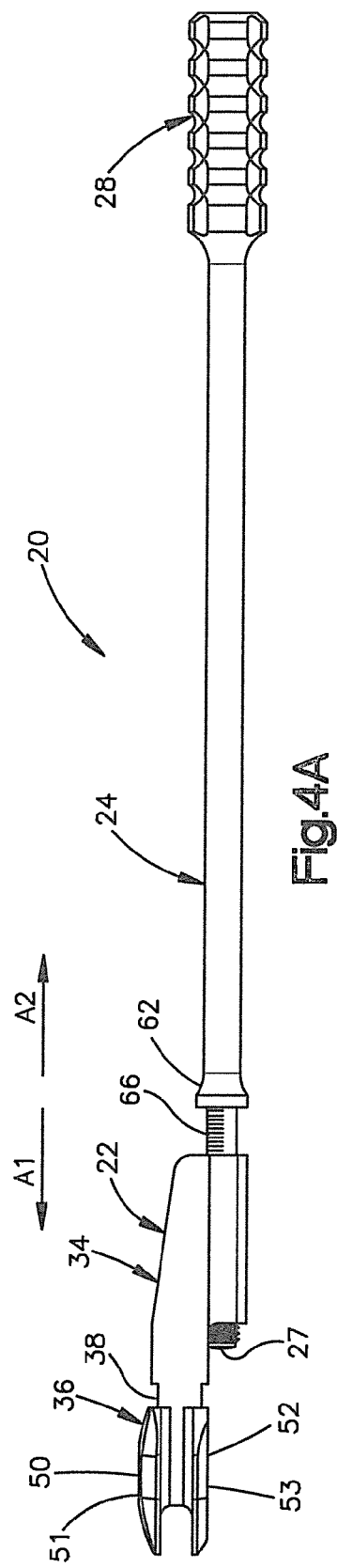
FIG. 4A is a side elevation view of the trial implant assembly similar to FIG. 2C, but showing the trial implant in a translated position relative to the shaft.

Referring now also to FIG. 4A, rotation of the shaft 24 relative to the trial implant 22 causes the threads 42 of the shaft 24 and the threads 48 of the trial base 34 to ride along each other, thereby causing the trial implant 22 to translate longitudinally relative to the shaft 24. For instance, rotation of the shaft 24 in a first direction (e.g., counterclockwise) relative to the trial implant 22 causes trial implant 22 to translate distally in the longitudinal direction relative to the shaft 24 as indicated by Arrow A1, while rotation of the shaft 24 in a second opposite direction (e.g., clockwise) relative to the trial implant 22 causes the trial implant 22 to move proximally in the longitudinal direction relative to the shaft 24 as indicated by Arrow A2. FIG. 2C illustrates the trial head 36 in a retracted position relative to the shaft 24, while FIG. 4A illustrates the trial head 36 in an extended position relative to the shaft 24.

Figure 4B:
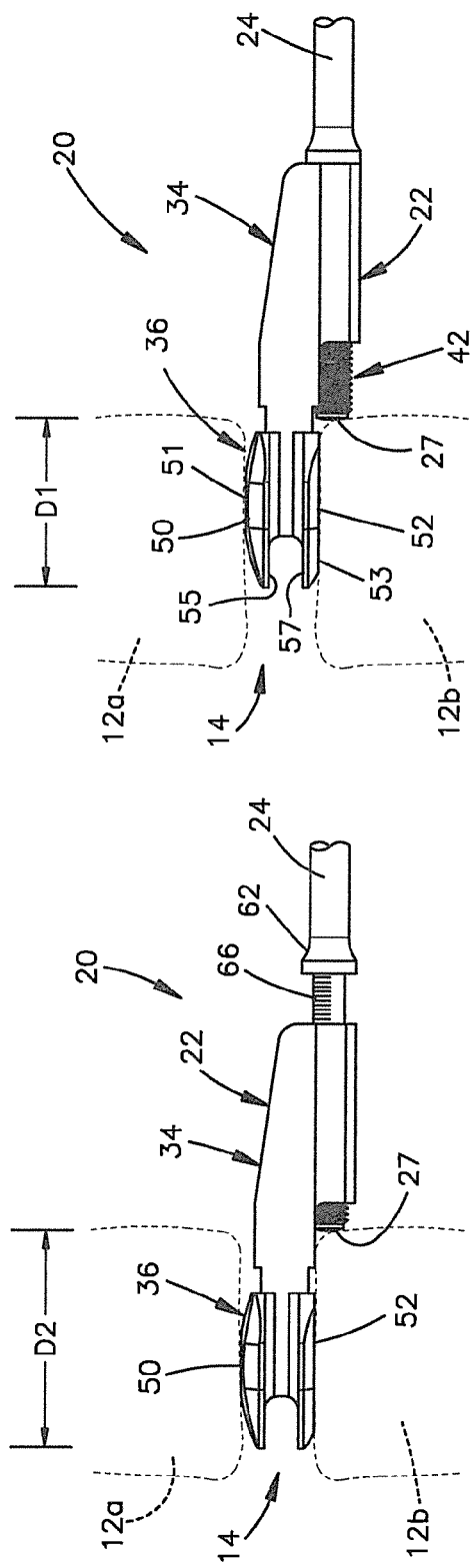
FIG. 4B is a side elevation view of the distal end of the trial implant assembly illustrated in FIG. 2C inserted into an intervertebral disc space at a first insertion depth.
Figure 4C:
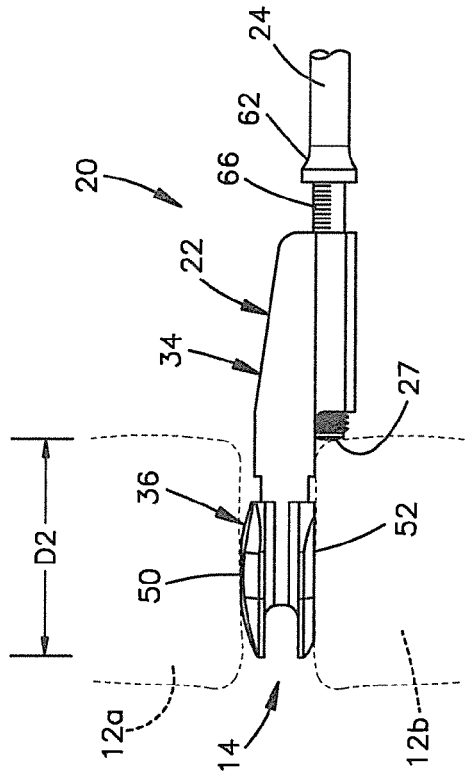
FIG. 4C is a side elevation view of the distal end of the trial implant assembly illustrated in FIG. 4A inserted into an intervertebral disc space at a second insertion depth that is different than the first insertion depth.

Furthermore, referring also to FIGS. 4B-C, at least a portion of the distal end 26b of the shaft body 26 is vertically offset from the trial head. In accordance with the illustrated embodiment, at least a portion of the distal end 26b of the shaft body 26 is disposed below the outer transverse surface 53 of the inferior endplate 52. Accordingly, the vertebral abutment surface 27 of the shaft 24 is configured to abut one of the vertebrae, such as the inferior vertebra 12b, when the trial head 36 is inserted into the intervertebral space 14. Accordingly, when the trial head 36 is in a retracted position as shown in FIG. 4B, the trial head 36 is inserted into the intervertebral disc space 14 at a first insertion depth D1 when the abutment surface 27 abuts the inferior vertebra 12b. When the trial head 36 is in an extended position as shown in FIG. 4C, the trial head 36 is inserted into the intervertebral disc space 14 at a second insertion depth D2 when the abutment surface 27 abuts the inferior vertebra 12b. The second insertion depth D2 is greater than the first insertion depth D1.

Referring again to FIG. 4A, the shaft 24 can include a stop member 62 that is configured to abut the proximal end of the trial base 34 when the trial implant 22 is fully retracted. The stop member 62 thus prevents the trial implant 22 from being retracted to a location where the threads 42 and 48 would become disengaged. The stop member 62 projects radially out from the shaft body 26 so as to define a cross-sectional dimension greater than that of the shaft body 26, and greater than that of the aperture 46 that receives the shaft body 26. The shaft 24 can include depth markings 66 or other indicia distal of the stop member 62 to indicate the position of the trial implant 22 relative the shaft 24.

Figure 5:
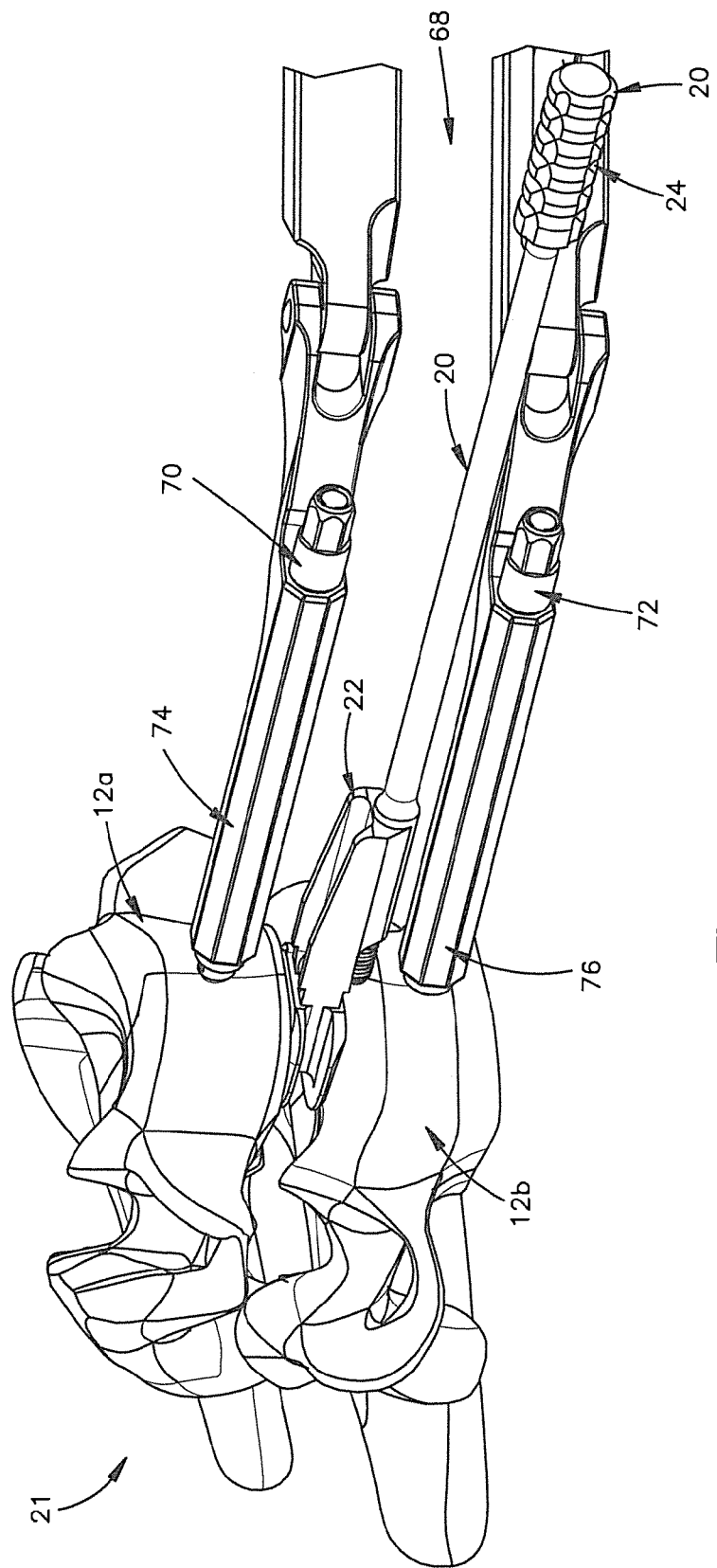
FIG. 5 is a perspective view of the trial implant assembly of FIG. 2 used in conjunction with a retainer distracter instrument and showing an anterior side of adjacent vertebrae.
Figure 6:
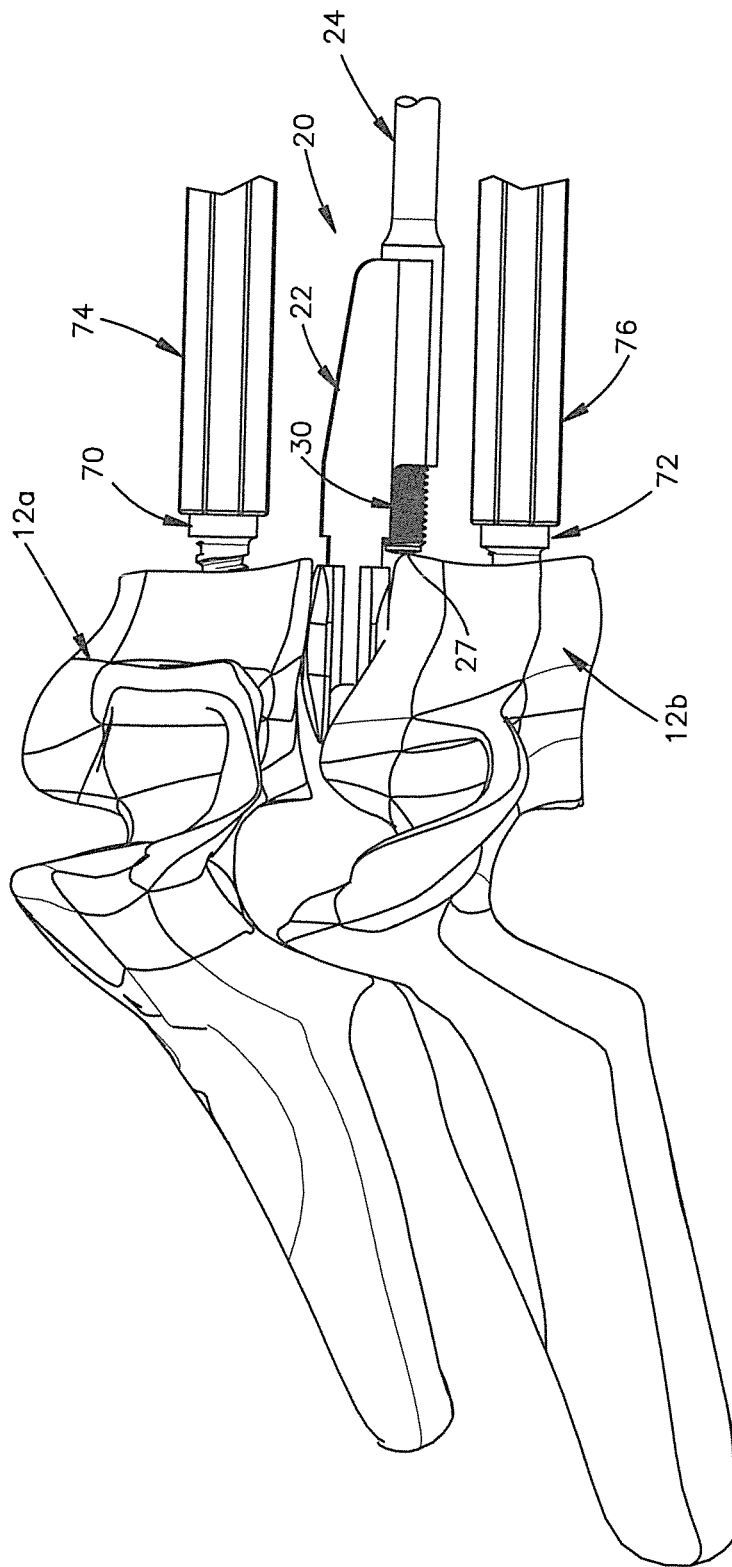
FIG. 6 is perspective view of the trial implant assembly illustrated in FIG. 5.
Figure 7:
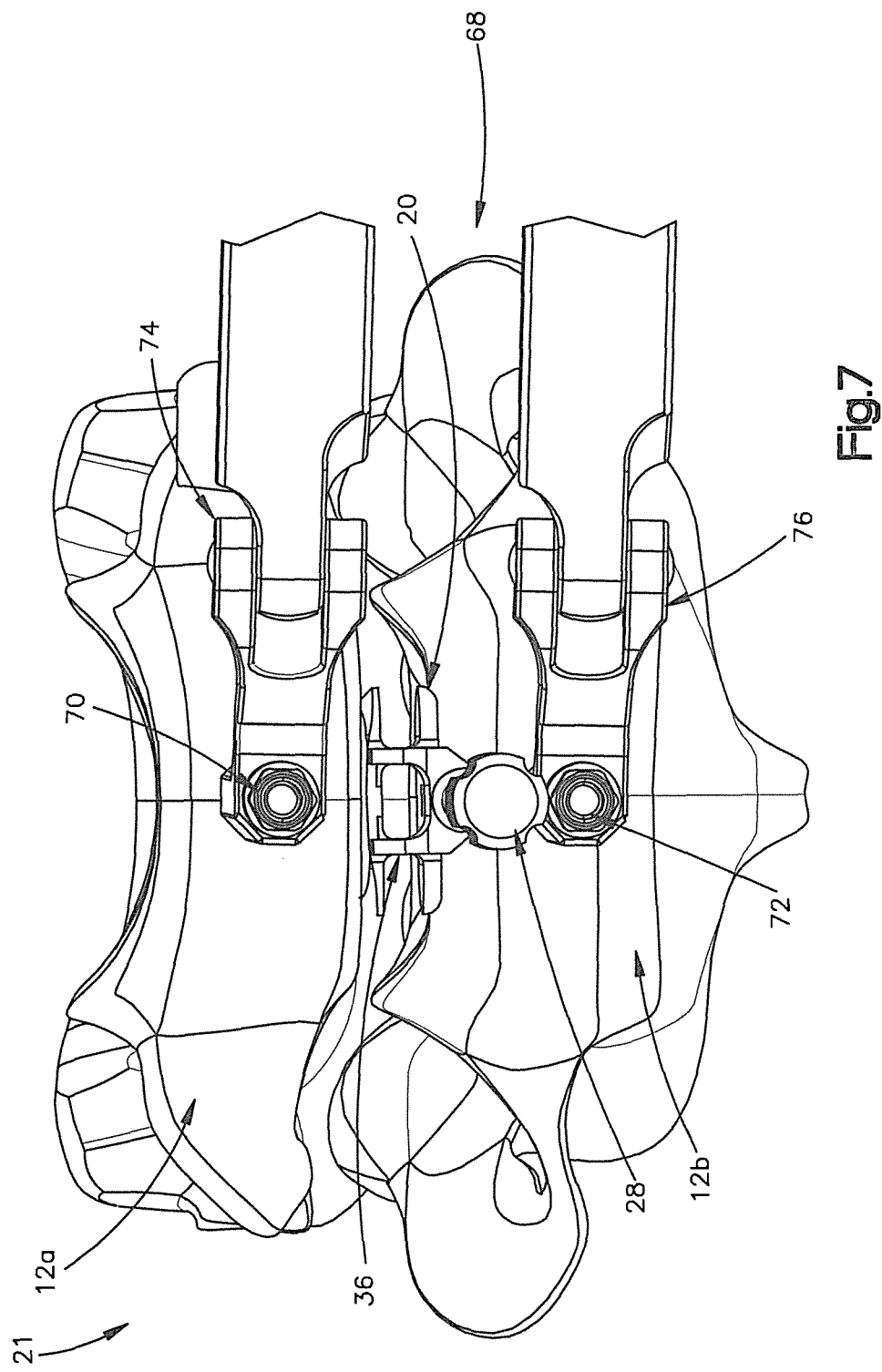
FIG. 7 is a proximal end elevation view of the trial implant assembly illustrated in FIG. 5.

Referring now also to FIGS. 5-7, an instrument assembly 21 can include the trial implant assembly 20 in combination with a distracter retainer instrument 68. The distracter retainer instrument 68 includes a superior anchor screw 70 configured to be temporarily driven or implanted into the superior vertebral body 12a, an inferior anchor screw 72 configured to be temporarily driven or implanted into the inferior vertebral body 12b. The distracter retainer instrument 68 further includes a superior retainer distracter tube 74 couplable to the superior anchor screw 70, and an inferior retainer distracter tube 76 couplable to the inferior anchor screw 72. The distracter retainer instrument 68 can be implemented to initially separate the superior and inferior vertebral bodies 12a and 12b, respectively, and retain distraction prior to cleaning out the disc tissue and inserting the total disc replacement implant. The anchor screws 70 and 72 can be removed from the vertebral bodies 12a and 12b after the permanent disc implant has been implanted between the vertebral bodies 12a and 12b.

During operation, and with continuing reference to FIGS. 1-7, at least a partial discectomy is performed and the intervertebral disc space 14 is decompressed, for instance using the distracter retainer instrument 68. A surgeon selects a trial head 36 to assess the size of the disc space 14 and couples the trial head 36 to the shaft 24. In particular, the threaded region 44 of the shaft 24 is inserted into the aperture 46 of the trial base 34, and the shaft 24 is rotated relative to the trial base 34 so that the threads 42 of the shaft 24 mate with the threads 48 of the trial base 34. The shaft 24 is continuously rotated relative to the trial head 34 until the trial implant 22 is fully retracted with respect to the shaft 24. Alternatively, the trial head could already be assembled to its own shaft with the head fully retracted.

The surgeon can insert the trial head 36 into the intervertebral disc space 14, for instance by tapping on the proximal end of shaft 24 with a small mallet to advance the trial head 36 into the intervertebral disc space 14 until the abutment surface 27 abuts the inferior vertebral body 12b. Should the surgeon wish to place the trial head 36 deeper within the disc space 14 the shaft 24 can be rotated in a counter clockwise direction, causing it to back out of trial base 34. Because the pitch of the thread 44 on shaft 24 is fixed, the surgeon can precisely control how much the shaft backs out. The trial head 36 can then be inserted deeper into the intervertebral disc space 14 by tapping on the proximal end of the shaft 24 until the abutment surface 27 contacts the vertebral body 12b again. The optional depth markings 66 can assist in determining the desired insertion depth of the trial head 36 in the disc space 14.

As the trial head 36 is inserted into the disc space 14, the visualization window 60 and the lateral slots 39 and 41 allow the surgeon to visually determine the position of the trial head 36 without using fluoroscopy or other radio imaging. More particularly, the window 60 allows for visualization of the posterior longitudinal ligament (PLL), while the first and second lateral slots 39 and 41 allow for visualization of the exiting nerve roots. Accordingly, as described above with respect to the visualization window, at least a portion up to all of the lateral slots 39 and 41 are visually unobstructed. In this regard, the visualization window 60 can define a primary visualization window, while the lateral slots 39 and 41 can define auxiliary visualization windows disposed adjacent the primary visualization window 60. Thus, at least one rib, such as ribs 38 and 40, can define at least one visualization window, such as visualization windows 60, 39, and 41.

Once the trial head 36 is positioned appropriately within the disc space 14, the surgeon assesses the fit of the trial head 36 within the disc space 14. If the trial head 36 is not properly sized for the disc space, the surgeon removes and replaces the trial head 36 with a differently sized trial head 36 and repeats the evaluation process. Once the properly size trial head 36 is in place, the trial head 36 is removed and a permanent total disc replacement implant having a size corresponding to the properly sized trial head 36 is permanently implanted in the disc space.

It should thus be appreciated that a kit can be provided that includes a plurality of trial implants 22, each couplable to the shaft 24, and each having trial heads 36 of incrementally larger volumes that are sized and configured to fill and provide the desired spacing between the superior and inferior vertebral bodies 12a and 12b. For instance, the trial heads 36 can define at least one or a plurality of varying characteristics, including a shape and/or a dimension such an outer lateral dimension, an outer longitudinal dimension, and a height between the outer transverse engagement surfaces 51 and 53. The trial head 36 of each trial implant 22 can be color coded, such as anodized or otherwise colored, such that a range of different colors is provided to distinguish between the range of different sizes of the corresponding trial heads 36.

It should be appreciated that the trial implant assembly 20 has been described in accordance with one embodiment, and that the trial implant assembly 20 could alternatively be constructed in accordance with numerous alternative embodiments that provide at least one visualization window. Some of the alternative embodiments are described below, it being appreciated that the scope of the present disclosure is not intended to be limited to any or all of the specific embodiments described herein.

For instance, referring to FIGS. 8A-D, a trial implant assembly 120 constructed in accordance with an alternative embodiment is illustrated including reference numerals corresponding to like elements of the trial implant assembly 20 incremented by 100. Thus, the trial implant assembly 120 can be constructed substantially as described with respect to the trial implant assembly 20 except as otherwise noted.

Figure 8D:
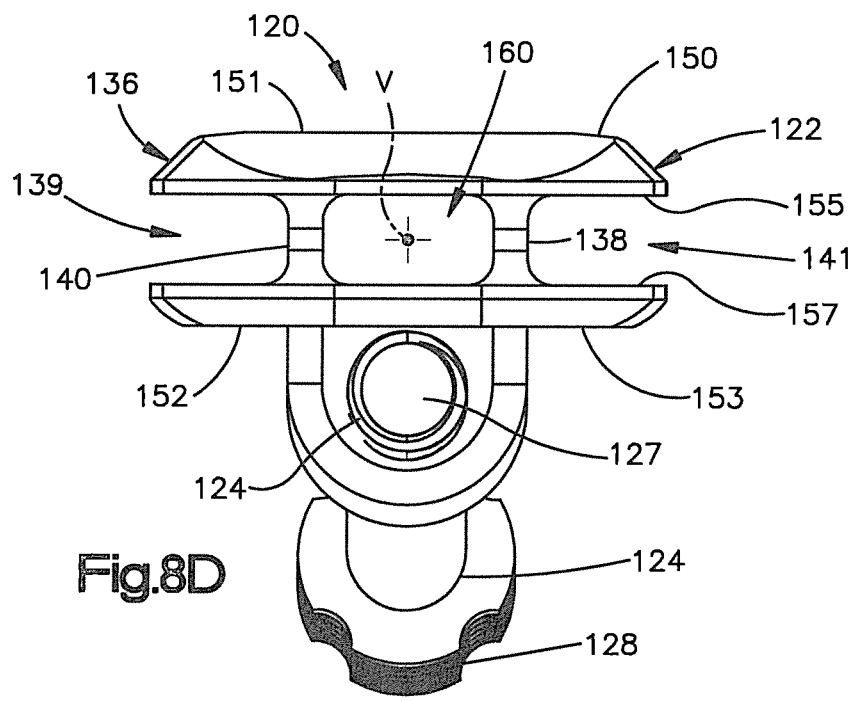
FIG. 8D is a distal end elevation view of the distal portion of the trial implant assembly illustrated in FIG. 8A.
Figure 8E:
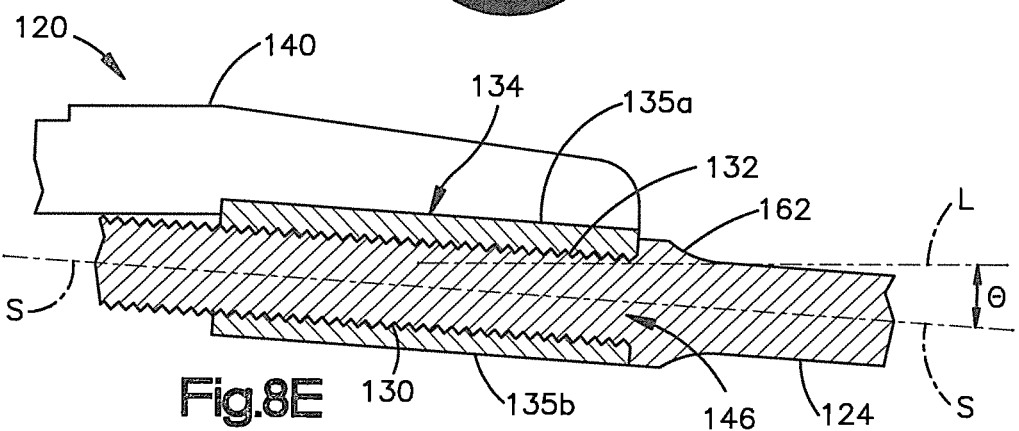
FIG. 8E is a sectional side elevation view of the angularly offset shaft as illustrated in FIG. 8B constructed in accordance with one embodiment.
Figure 8F:
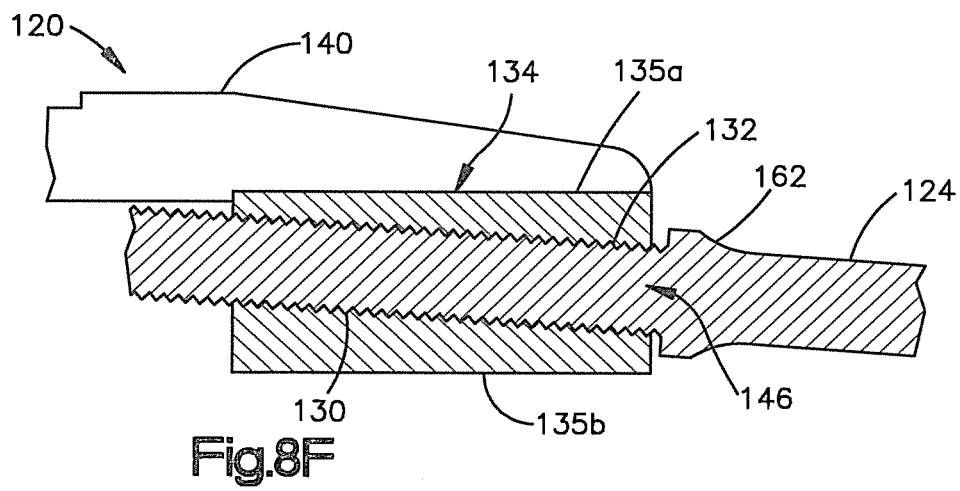
FIG. 8F is a sectional side elevation view of the angularly offset shaft as illustrated in FIG. 8B constructed in accordance with another embodiment.
Figure 11A:
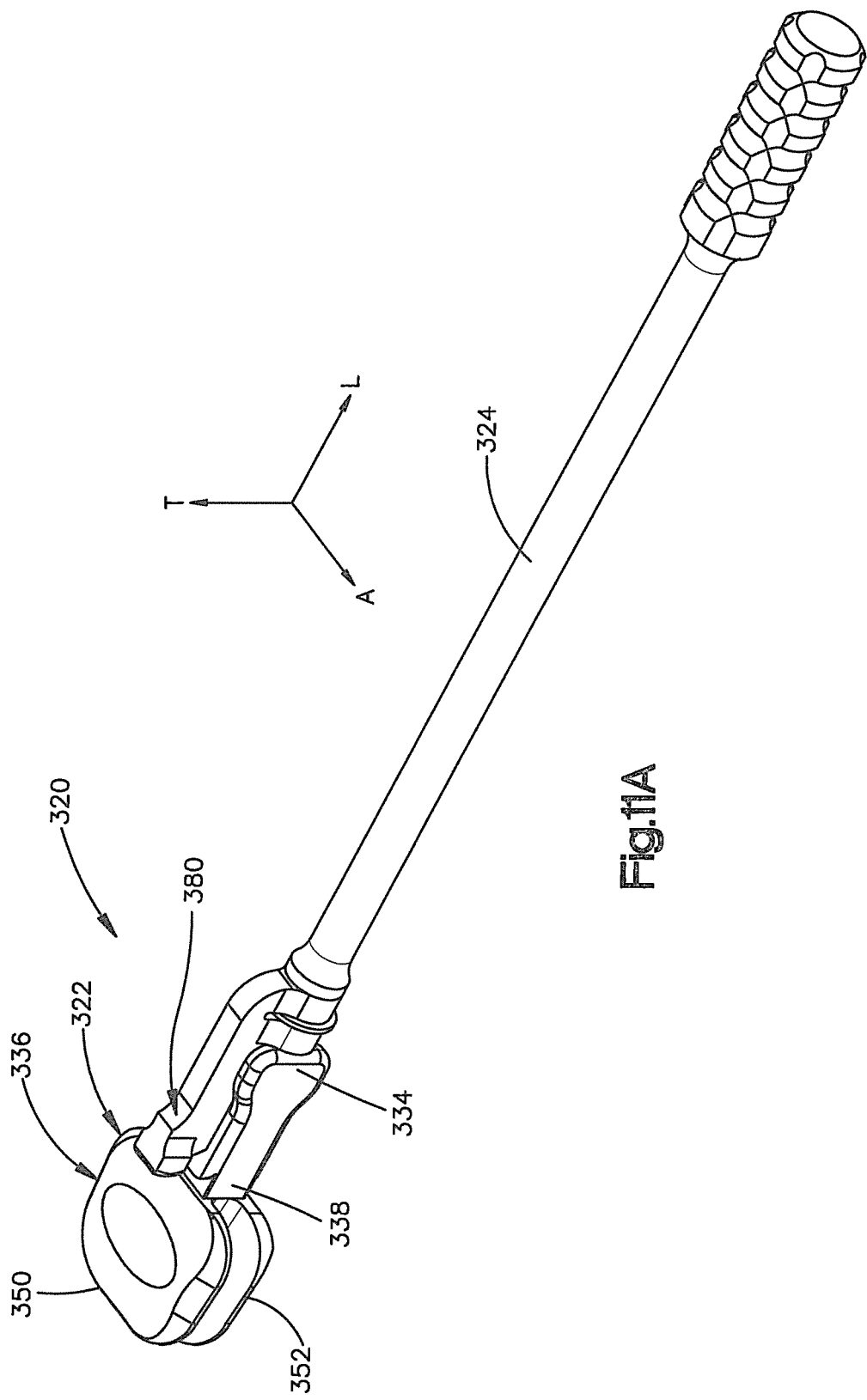
FIG. 11A is a perspective view of a trial implant assembly in accordance with an alternative embodiment.
Figure 11D:
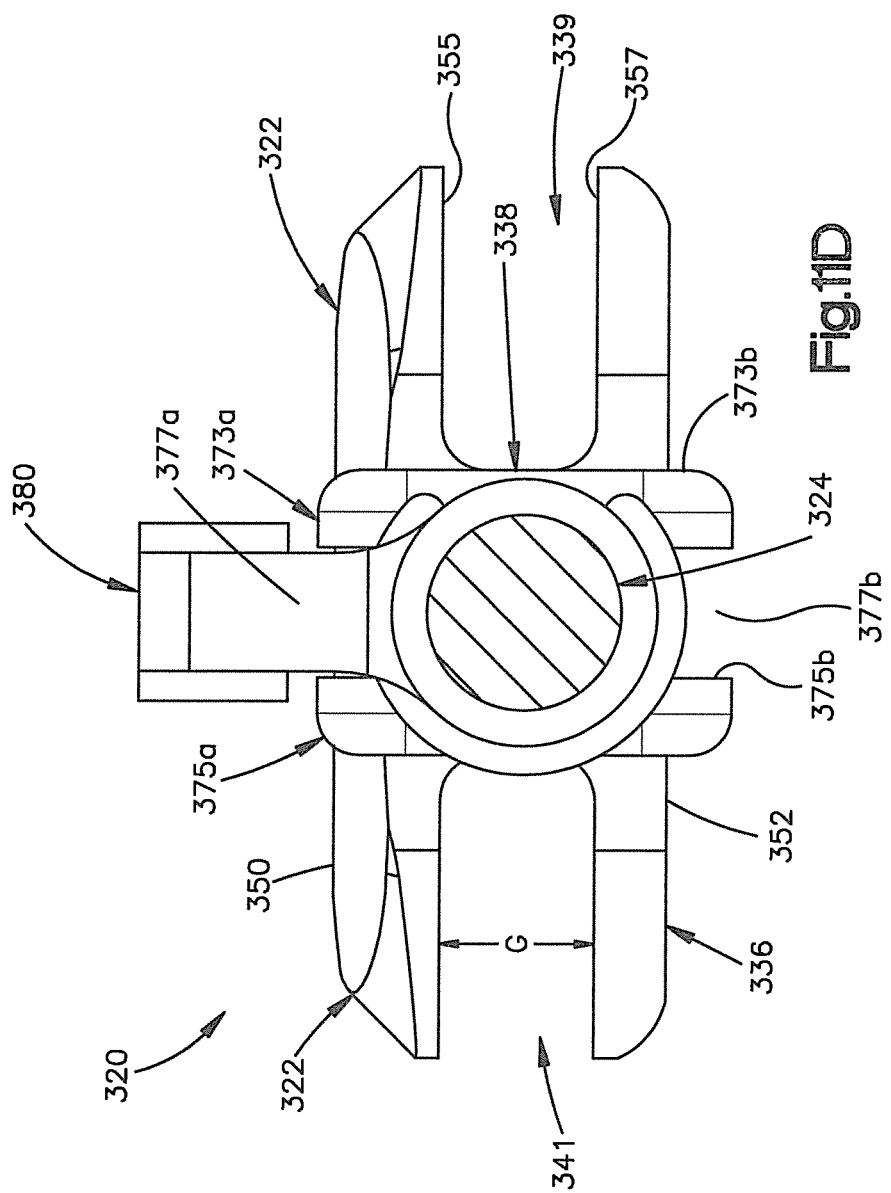
FIG. 11D is a sectional distal end elevation view of the trial implant assembly illustrated in FIG. 11A.
Figure 12A:
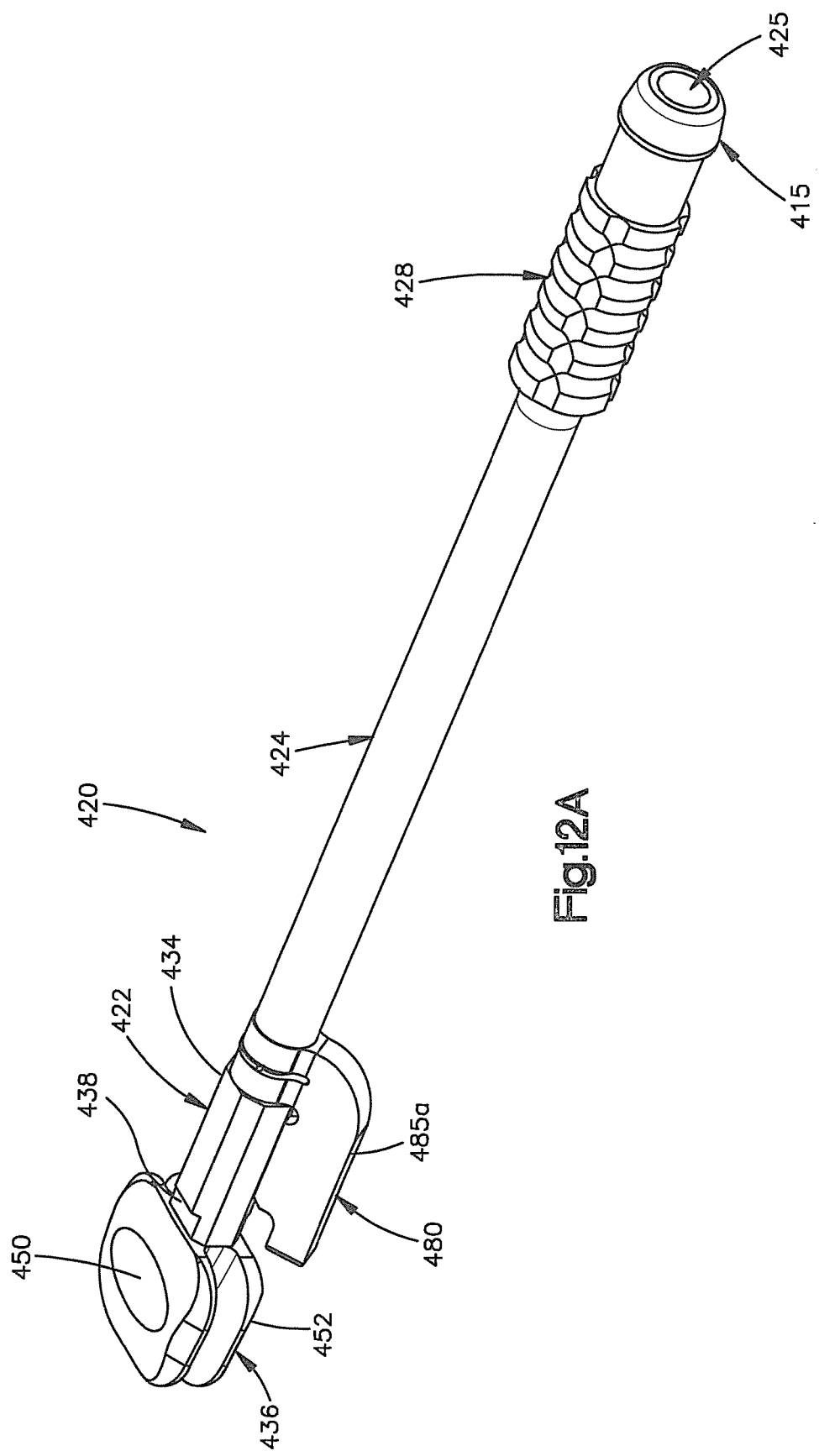
FIG. 12A is a perspective view of a trial implant assembly including a shaft and a trial implant in accordance with an alternative embodiment.
Figure 14A:
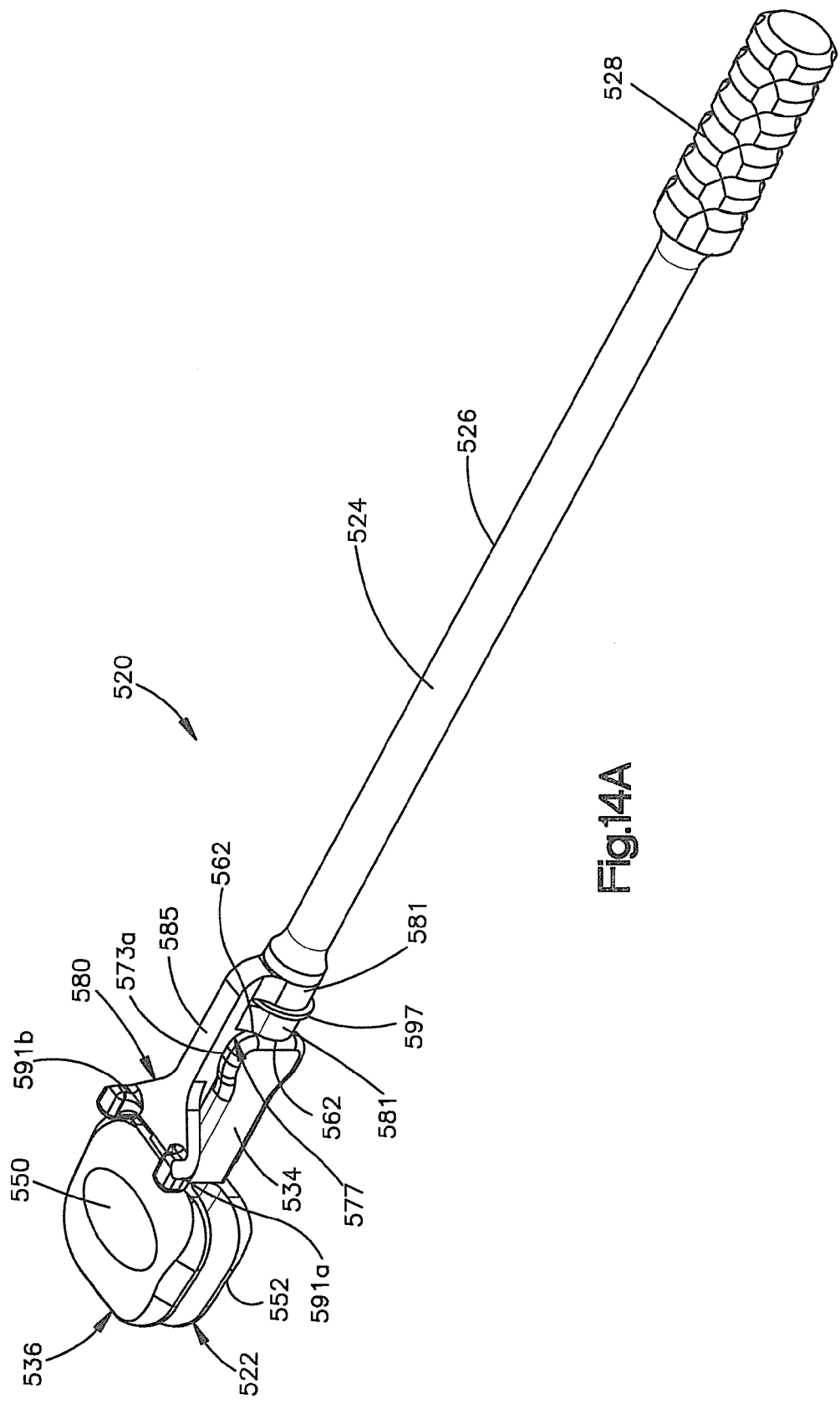
FIG. 14A is a perspective view of a trial implant assembly constructed in accordance with an alternative embodiment.

As described above and illustrated with respect to FIGS. 2-4C, the shaft 24 of the trial implant assembly 20 can extend longitudinally, or perpendicular to the transverse direction T. As illustrated in FIGS. 8A-D, it is further recognized that the shaft 124 can extend in a direction angularly offset with respect to the longitudinal direction L, and thus with respect to the visualization window 160 that extends longitudinally through the trial head 136. In accordance with the illustrated embodiment, the shaft 124 is angled transversely downward with respect to the longitudinal direction L so as to define an angle θ with respect to the longitudinal direction L that can be any angle as desired, such as between 0° and 60°. Thus, the central shaft axis S can extend at a non-perpendicular angle with respect to the transverse axis T. As illustrated in FIG. 8E, the trial base 134 can oriented such that the upper and lower surfaces 135a and 135b extend parallel to the central shaft axis S, and the aperture 146 that receives the shaft 124 extends parallel to the upper and lower surfaces 135a and 135b as illustrated in FIG. 2D. Alternatively, as illustrated in FIG. 8F, upper and lower surfaces 135a and 135b can extend longitudinally, and thus angularly offset with respect to the central shaft axis S, and the aperture 146 that receives the shaft 124 can extend through the trial base in a direction that is angularly offset with respect to the upper and lower surfaces 135a and 135b so as to receive the shaft 124 along the angularly offset shaft axis S.

Referring now to FIGS. 9A-10C, a trial implant assembly 220 constructed in accordance with an alternative embodiment is illustrated including reference numerals corresponding to like elements of the trial implant assembly 20 incremented by 200. Thus, the trial implant assembly 220 can be constructed substantially as described with respect to the trial implant assembly 20 except as otherwise noted. As illustrated, the trial implant assembly 220 includes the shaft 224, and a trial implant 222 configured to be removably coupled to the shaft 224. The trial implant 222 includes a trial head 226 having a superior endplate 250 and an inferior endplate 252 configured to be inserted into an intervertebral space, a trial base 234 configured to be coupled to the shaft 224, and laterally spaced ribs 238 and 240 connected between the trial head 236 and the trial base 234 as described above. Thus, the ribs 238 and 240 are spaced so as to provide a primary visualization window 260 and auxiliary visualization window in the form of first and second laterally opposed slots 239 and 241, as described above.

The trial base 234 includes a trial base body 235 that defines a pair of laterally or horizontally spaced engagement members 232a-b that are each configured to connect to a complementary engagement member 230 of the shaft 224. In particular, the engagement member 230 of the shaft 224 is illustrated as including external threads 242 disposed in a threaded region 244 proximate to the distal end of the shaft 226. The engagement members 232a-b each includes a corresponding pair of laterally spaced apertures 246a-b that each extends longitudinally through the trial base 234. The apertures 246a-b are each sized to receive the threaded region 244 of the shaft 224. The engagement members 232a-b of the trial base 234 includes internal threads 248 disposed about the periphery of the apertures 246a-b that are configured to mate with the external threads 242 of the shaft 224 so as to couple the shaft 224 to the trial implant 222.

The apertures 246a-b are laterally offset on opposite sides with respect to a lateral midpoint of the primary visualization window 260. Each aperture 246a-b is further vertically or transversely offset with respect to a vertical or transverse midpoint of the primary visualization window 260. Furthermore, one or both of the apertures 246a-b can extend longitudinally, or can be angled with respect to the longitudinal direction L as described above. The trial base 234 thus defines a pair of offset engagement members 232a-b that are configured to be coupled to the shaft 224, such that the shaft 224 can be coupled to the trial implant 222 at multiple locations. In particular, the threaded region 244 of the shaft 224 can be mated with the threads 248 of either engagement member 232a-b so as to provide relative motion between the trial implant 222 and the shaft 224 in the manner described above.

Referring now to FIGS. 11A-D, a trial implant assembly 320 constructed in accordance with an alternative embodiment is illustrated including reference numerals corresponding to like elements of the trial implant assembly 20 incremented by 300. Thus, the trial implant assembly 320 can be constructed substantially as described with respect to the trial implant assembly 20 except as otherwise noted. As illustrated, the trial implant assembly 320 includes a shaft 324, which may or may not be cannulated, and a trial implant 322, which may or may not be cannulated, configured to be removably coupled to the shaft 324. The trial implant 322 includes a trial head 336 having a superior endplate 350 and an inferior endplate 352 configured to be inserted into an intervertebral space, a trial base 334 configured to be coupled to the shaft 324, and a laterally central rib 338 connected between the trial head 336 and the trial base 334.

The superior endplate 350 defines a lower or inferior, or inner transverse, surface 355, and the inferior endplate 352 defines an upper or superior, or inner transverse, surface 357. The surfaces 355 and 357 are spaced vertically along the transverse direction T by a gap G as illustrated, though it should be appreciated that the endplates 350 and 352 could alternatively be connected at their inner transverse ends. The rib 338 extends distally from the trial base 334, and is connected between the surfaces 355 and 357 of the endplates 350 and 352, respectively. First and second laterally opposed visualization slots 339 and 341 extend longitudinally through the trial head 336 on opposed lateral sides of the rib 338. The distal end of the rib 338 can terminate proximal to the distal end of the trial head 336, or endplates 350 and 352, so as to provide increased visualization and allow improved access to posterior structures in the disc space using a conventional nerve hook or probe.

The trial base 334 defines an engagement member 332 that is configured to connect to the engagement member 330 of the shaft 324. The trial implant 322 includes an aperture 346 that extends longitudinally through the trial base body 335, and can further extend longitudinally through the rib 338. The aperture 346 is sized to receive the threaded region 344 of the shaft 324. The engagement member 332 of the trial base 334 includes internal threads 348 disposed about the periphery of the aperture 346 that are configured to mate with the external threads 342 of the shaft 324 so as to couple the shaft 324 to the trial implant 322.

The trial base 322 further includes a pair of superior tracks 373a and 375a extending up, or transversely out, from the superior or upper surface 335a of the trial base body 335, and a pair of inferior tracks 373b and 375b extending down, or transversely out, from the lower or inferior surface 335b of the trial base body 335. The superior tracks 373a and 375a are laterally spaced from each other so as to define a superior longitudinally elongate guide channel 377a extending between the superior tracks 373a and 375a. The inferior tracks 373b and 375b are laterally spaced from each other so as to define an inferior longitudinally elongate guide channel 377b extending between the inferior tracks 373b and 375b.

The shaft 324 includes an adjustable mechanical stop 380 coupled to the distal portion of the shaft body 326 such that the stop 380 is rotatable with respect to the shaft body 326 but is translatably fixed relative to the shaft 324. Thus, the stop 380 can rotate about the shaft body 326 but is unable to translate along the shaft body 326. In particular, the stop 380 includes at least one circumferential collar 381 (a pair of longitudinally spaced collars 381 are illustrated) that nest within a corresponding at least one radial groove 383 (a pair of longitudinally spaced grooves 383 are illustrated) that extend into the shaft body 326. Interference between the collars 381 and the portion of the shaft body 326 that is adjacent the grooves 383 prevent the stop 380 from translating along the shaft body 326. Alternatively, a snap ring can be snapped onto the shaft 324 into a groove disposed between the collars 381, such that the interference between the snap ring and the collars 381 prevent translation of the stop 380 along the shaft 324. The collars 381, and thus the stop 380, are free to rotate about the shaft body 326 within the radial grooves 383.

The distal surface of the distal-most collar 381 defines a stop member 362 configured to abut the proximal end of the trial base 334 when the trial implant 322 is fully retracted on the shaft 324. The stop member 362 thus prevents the trial implant 322 from being retracted to a location where the threads 342 and 348 would become disengaged. The stop member 362 projects radially out from the shaft body 326 so as to define a cross-sectional dimension greater than that of the shaft body 326, and greater than that of the aperture 346 that receives the shaft body 326.

The stop 380 further includes a guide body 385 extending transversely outward and longitudinally distal from the collars 381. The guide body 385 defines a lateral outer dimension substantially equal to or slightly less than that of the guide channels 377a-b. Accordingly, the guide body 385 is configured to ride within and translate within a select one of the guide channels 377a-b as the shaft 324 is rotated relative to the trial base 334, thereby causing the implant 322 to translate relative to the shaft 324.

The stop 380 further defines a vertebral abutment surface 327 defined by the distal surface of the guide body 385. When the guide body 385 is disposed in the superior guide channel 377a, the abutment surface 327 is configured to abut the superior vertebra when the trial head 336 is inserted into the intervertebral space. When the guide body 385 is disposed in the inferior guide channel 377b, the abutment surface 327 is configured to abut the inferior vertebra when the trial head 336 is inserted into the intervertebral space. Thus, the guide channels 377a-b are configured to maintain the alignment of the vertebral abutment surface 327 with a select one of the superior and inferior vertebrae based on the anatomy of the patient. Once the trial head 336 is positioned within the intervertebral disc space, the shaft 324 can be uncoupled, i.e., unscrewed, from the trial implant 322 and the aperture 346 can serve as a primary visualization window into the intervertebral disc space as described above with respect to the primary visualization window 60. The shaft 324 can further be cannulated, such that the cannulation of the shaft 324 is aligned with the aperture 346. Accordingly, the visualization window defined by the aperture 346 can be visually accessed through the cannulation of the shaft 324.

Referring now to FIGS. 12A-13B, a trial implant assembly 420 constructed in accordance with an alternative embodiment is illustrated including reference numerals corresponding to like elements of the trial implant assembly 20 incremented by 400. Thus, the trial implant assembly 420 can be constructed substantially as described with respect to the trial implant assembly 20 except as otherwise noted. As illustrated, the trial implant assembly 420 includes a shaft 424, and a trial implant 422 configured to be removably coupled to the shaft 424. The trial implant 422 includes a trial head 436 having a superior endplate 450 and an inferior endplate 452 configured to be inserted into an intervertebral space, a trial base 434 configured to be coupled to the shaft 424, and a laterally central rib 438 connected between the trial head 436 and the trial base 434.

The superior endplate 450 defines a lower or inferior, or inner transverse, surface 455, and the inferior endplate 452 defines an upper or superior, or inner transverse, surface 457. The surfaces 455 and 457 are spaced vertically along the transverse direction T by a gap G as illustrated, though it should be appreciated that the endplates 450 and 452 could alternatively be connected at their inner transverse ends. The rib 438 extends distally from the trial base 434, and is connected between the surfaces 455 and 457 of the endplates 450 and 452, respectively. First and second laterally opposed visualization slots 439 and 441 extend longitudinally through the trial head 336 on opposed lateral sides of the rib 438. The distal end of the rib 438 can terminate proximal to the distal end of the trial head 436, or endplates 450 and 452, so as to provide increased visualization and allow improved access to posterior structures in the disc space using a conventional nerve hook or probe. Furthermore, the laterally opposed outer walls of the rib 438 are concave and convergingly tapered along a direction from the proximal end of the rib 438 toward the distal end of the rib 438, thereby increasing visualization of the middle of the disc space.

The trial base 434 defines an engagement member 432 that is configured to connect to the engagement member 430 of the shaft 424. In particular, the trial implant 422 includes an aperture 446 that extends longitudinally through the trial base body 435, and further extends longitudinally through the rib 438. A portion of substantially all of aperture 446 is sized to receive the threaded region 444 of the shaft 424. The engagement member 432 of the trial base 434 includes internal threads 448 disposed about the periphery of part or all of the aperture 446 that are configured to mate with the external threads 442 of the shaft 424 so as to couple the shaft 424 to the trial implant 422.

The trial base 422 can further include a pair of superior tracks 473a and 475a (see FIG. 13D) that extend transversely out from, and flare laterally out from, the superior or upper surface 435a of the trial base body 435, and a pair of inferior tracks 473b and 475b that extend transversely out from, and flare laterally out from, the lower or inferior surface 435b of the trial base body 435. Thus, the tracks 473a and 475a flare laterally away from each other, and the tracks 473b and 475b flare laterally away from each other. The superior tracks 473a and 475a can be constructed substantially as described with respect to the inferior tracks 475b and 475b illustrated in FIGS. 12A-13C, except that the superior tracks 473a and 475a are transversely inverted with respect to the inferior tracks 473b and 475b.

The shaft 424 defines a cannulation 425 that extends longitudinally through the shaft body 426. The proximal portion of the shaft 424 includes a mechanism 415 for connecting to tubing for siphoning out blood and/or other tissue or debris remaining from the discectomy as described below.

The shaft 424 further includes an adjustable mechanical stop 480 coupled to the distal portion of the shaft body 426 such that the stop 480 is rotatable with respect to the shaft body 426 but is translatably fixed relative to the shaft 424. Thus, the stop 480 can rotate about the shaft body 426 but is unable to translate along the shaft body 426. In particular, the stop 480 includes at least one circumferential collar 481 (a pair of longitudinally spaced collars 481 are illustrated) that nest within a corresponding at least one radial groove 483 (a pair of spaced grooves 483 are illustrated) that extend into the shaft body 426. Interference between the collars 481 and the portion of the shaft body 426 that is adjacent the grooves 483 prevent the stop 480 from translating along the shaft body 426. Alternatively, a snap ring can be snapped onto the shaft 424 into a groove disposed between the collars 481, such that the interference between the snap ring and the collars 481 prevent translation of the stop 480 along the shaft 424. The collars 481, and thus the stop 480, are free to rotate about the shaft body 426 within the radial grooves 483.

The distal surface of the distal-most collar 481 defines a stop member 462 configured to abut the proximal end of the trial base 434 when the trial implant 422 is fully retracted on the shaft 424. The stop member 462 thus prevents the trial implant 422 from being retracted to a location where the threads 442 and 448 would become disengaged. The stop member 462 projects radially out from the shaft body 426 so as to define a cross-sectional dimension greater than that of the shaft body 426, and greater than that of the aperture 446 that receives the shaft body 426.

The stop 480 is forked with a first guide body 485a and a second guide body 485b that flare laterally away from each other along a transversely outward direction. Each of the first and second guide bodies 485a-b are positioned such that the laterally inner surfaces of the guide bodies 485a-b ride along the laterally outer surfaces of the superior tracks 473a and 475a when the guide bodies 485a-b are aligned with the superior tracks, and ride along the laterally outer surfaces of the inferior tracks 473b and 475b when the guide bodies 485a-b are aligned with the inferior tracks. In particular, each guide body 485a and 485b can include a pocket 487a and 487b, respectively, that at least partially receives the corresponding track 473 and is configured to ride along the track 473.

During operation, the stop 480 is rotated about the shaft 424 as desired so as to align the stop 480 with a select one of the superior tracks 473a and 475a, and the inferior tracks 473b and 475b. The threads 442 of the shaft 424 are then engaged with the threads 448 of the trial implant 422, which causes the guide bodies 485a-b to ride along the selected tracks 473 and 475. Accordingly, the guide bodies 485 are configured to ride along the tracks 473 and 475 as the shaft 324 424 is rotated relative to the trial base 434, thereby causing the trial implant 422 to translate relative to the shaft 424. The space between the first and second guide bodies 485a-b allow the trial implant 422 to be placed around or in close proximity to a Caspar distraction pin or various elements of the distracter 68 as described above with respect to FIGS. 5-7.

The stop 480 further defines a vertebral abutment surface 427 defined by the distal surface of the guide body 485. When the guide body 485 engages the superior tracks 473a and 475a, the abutment surface 427 is configured to abut the superior vertebra when the trial head 436 is inserted into the intervertebral space. When the guide body 485 engages the inferior tracks 473b and 475b, the abutment surface 427 is configured to abut the inferior vertebra when the trial head 436 is inserted into the intervertebral space. Thus, the tracks 473 and 475 are configured to maintain the alignment of the vertebral abutment surface 427 with a select one of the superior and inferior vertebrae based on the anatomy of the patient. Once the trial head 436 is positioned within the intervertebral disc space, the shaft 424 can be uncoupled, i.e., unscrewed, from the trial implant 422 and the aperture 446 can serve as a primary visualization window into the intervertebral disc space as described above with respect to the primary visualization window 60. The cannulation 425 of the shaft 424, which is in alignment with the aperture 446, provides visual access to the visualization window defined by the aperture 446 prior to removal of the shaft 424 from the trial implant 422. The cannulation 425 of the shaft 424 further allows blood and other matter to be siphoned out from the disc space.

Once the trial head 436 is inserted into the disc space, a vacuum source (not shown) is connected to the connection mechanism 415 on the proximal end of the shaft 424 and suction is applied to remove debris, such as blood and/or tissue debris remaining from the discectomy from the disc space, through the through hole 425, and out through the cannulated interior of the shaft 424. Thus, the cannulated shaft can provide a suction passageway for the removal of debris under an applied vacuum pressure. The removal of tissue debris and blood increases visualization and, further, provides a better suited intervertebral environment for implantation of the total disc replacement implant.

Referring now to FIGS. 14A-E, a trial implant assembly 520 constructed in accordance with an alternative embodiment is illustrated including reference numerals corresponding to like elements of the trial implant assembly 20 incremented by 500. Thus, the trial implant assembly 520 can be constructed substantially as described with respect to the trial implant assembly 20 except as otherwise noted. As illustrated, the trial implant assembly 520 includes a shaft 524, and a trial implant 522 configured to be removably coupled to the shaft 524. The trial implant 522 includes a trial head 536 having a superior endplate 550 and an inferior endplate 552 configured to be inserted into an intervertebral space, a trial base 534 configured to be coupled to the shaft 524, and a laterally central rib 538 connected between the trial head 536 and the trial base 534.

The superior endplate 550 defines a lower or inferior, or inner transverse, surface 555, and the inferior endplate 552 defines an upper or superior, or inner transverse, surface 557. The surfaces 555 and 557 are spaced vertically along the transverse direction T by a gap G as illustrated, though it should be appreciated that the endplates 550 and 552 could alternatively be connected at their inner transverse ends. The rib 538 extends distally from the trial base 534, and is connected between the surfaces 555 and 557 of the endplates 550 and 552, respectively. First and second laterally opposed visualization slots 539 and 541 extend longitudinally through the trial head 536 on opposed lateral sides of the rib 538. The distal end of the rib 538 can terminate proximal to the distal end of the trial head 536, or endplates 550 and 552, so as to provide increased visualization and allow improved access to posterior structures in the disc space using a conventional nerve hook or probe.

The trial base 534 further includes a pair of superior tracks 573a and 575a extending up, or transversely out, from the superior or upper surface 535a of the trial base body 535, and a pair of inferior tracks 573b and 575b extending down, or transversely out, from the lower or inferior surface of the trial base body 535. The superior tracks 573a and 575a are laterally spaced from each other so as to define a superior longitudinally elongate guide channel 577a extending between the superior tracks 573a and 575a. The inferior tracks 573b and 575b are laterally spaced from each other so as to define an inferior longitudinally elongate guide channel 577b extending between the inferior tracks 573b and 575b.

The shaft 524 includes an adjustable mechanical stop 580 coupled to the distal portion of the shaft body 526 such that the stop 580 is rotatable with respect to the shaft body 526 but is translatably fixed relative to the shaft body 526. Thus, the stop 580 can rotate about the shaft body 526 but is unable to translate along the shaft body 526. In particular, the stop 580 includes a pair of longitudinally spaced collars 581. The shaft 524 includes a snap ring 597 that is disposed in a groove 583 extending into the shaft body 526, such that the ring 597 is disposed between the collars 581. Thus, interference between the ring 597 and the collars 581 prevent translation of the stop 580 along the shaft 524. The collars 581, and thus the stop 580, are free to rotate about the shaft body 526.

The distal surface of the distal-most collar 581 defines a stop member 562 configured to abut the proximal end of the trial base 534 when the trial implant 522 is fully retracted on the shaft 524. The stop 580 further includes a guide body 585 extending transversely outward and longitudinally distal from the collars 581. The guide body 585 defines a lateral outer dimension substantially equal to or slightly less than that of the guide channels 577a-b. Accordingly, the guide body 585 is configured to ride within and translate within a select one of the guide channels 577a-b as the shaft 524 is rotated relative to the trial base 534, thereby causing the trial implant 522 to translate relative to the shaft 524 in the manner described above.

The stop 580 further defines a pair vertebral abutment surfaces 527a-b defined by the distal surface of the guide body 585. In particular, the guide body 585 defines a pair of legs 591a-b that extend forward from the guide body 585. The legs 591a-b are laterally separated from each other. Thus, the vertebral abutment surfaces 527 a-b are defined by the distal surfaces of the legs 591a-b, such that a gap 593 extends laterally between the abutment surfaces 527a-b. The abutment surfaces 527a-b are configured to abut the same vertebra when the trial head 536 is inserted into an intervertebral space.

For instance, when the guide body 585 is disposed in the superior guide channel 577a, the abutment surfaces 527a-b are configured to abut the superior vertebra when the trial head 536 is inserted into the intervertebral space. When the guide body 585 is disposed in the inferior guide channel 577b, the abutment surfaces 527a-b are configured to abut the inferior vertebra when the trial head 536 is inserted into the intervertebral space. Thus, the guide channels 577a-b are configured to maintain the alignment of the vertebral abutment surface 527 with a select one of the superior and inferior vertebrae based on the anatomy of the patient.

Referring now to FIGS. 15A-E, a trial implant assembly 620 constructed in accordance with an alternative embodiment is illustrated including reference numerals corresponding to like elements of the trial implant assembly 520 incremented by 100. Thus, the trial implant assembly 620 can be constructed substantially as described with respect to the trial implant assembly 520 except as otherwise noted. As illustrated, the trial implant assembly 620 includes a shaft 624, and a trial implant 622 configured to be removably coupled to the shaft 624. The trial implant 622 includes a trial head 636 having a superior endplate 650 and an inferior endplate 652 configured to be inserted into an intervertebral space, a trial base 634 configured to be coupled to the shaft 624, and a laterally central rib 638 connected between the trial head 636 and the trial base 634.

The stop 680 includes a guide body 685 extending transversely outward and longitudinally distal from the collars 681. The guide body 685 defines a lateral outer dimension substantially equal to or slightly less than that of the guide channels 677a-b. Accordingly, the guide body 685 is configured to ride within and translate within a select one of the guide channels 677a-b as the shaft 624 is rotated relative to the trial base 634, thereby causing the trial implant 622 to translate relative to the shaft 624 in the manner described above.

The stop 680 further defines a pair vertebral abutment surfaces 627a-b defined by the distal surface of the guide body 685. In particular, the guide body 685 defines a pair of superior and inferior legs 691a-b that extend forward from the guide body 685, and are transversely separated from each other Thus, the vertebral abutment surfaces 627a-b are defined by the distal surfaces of the legs 691a-b, such that the abutment surfaces 627a-b are transversely separated. Thus, the abutment surfaces 627a-b are configured to abut different vertebrae when the trial head 636 is inserted into an intervertebral space. Specifically, the abutment surfaces 627a-b are configured to abut the adjacent vertebrae that define the intervertebral space into which the trial head 636 is inserted. Thus, the superior abutment surface 627a is configured to abut the superior vertebra, and the inferior abutment surface 627b is configured to abut the inferior vertebra. It should be appreciated that the superior and inferior legs 691a-b could be split so as to each define a pair of vertebral abutment surfaces in the manner illustrated in FIGS. 14A-D.

Referring now to FIGS. 16A-E, a trial implant assembly 720 constructed in accordance with an alternative embodiment is illustrated including reference numerals corresponding to like elements of the trial implant assembly 520 incremented by 200. Thus, the trial implant assembly 720 can be constructed substantially as described with respect to the trial implant assembly 520 except as otherwise noted. As illustrated, the trial implant assembly 720 includes a shaft 724, and a trial implant 722 configured to be removably coupled to the shaft 724. The trial implant 722 includes a trial head 736 having a superior endplate 750 and an inferior endplate 752 configured to be inserted into an intervertebral space, a trial base 734 configured to be coupled to the shaft 724, and a laterally central rib 738 connected between the trial head 736 and the trial base 734.

The stop 780 includes a guide body 785 extending radially outward and longitudinally distal from the collars 781. The stop 780 defines a channel 792 extending into the radially inner end of the guide body 785. The channel 792 can extend longitudinally through the proximal end of the guide body 785, and can terminate prior to the distal end of the guide body, or can extend longitudinally through the distal end of the guide body. The trial base 734 further includes a track 773 extending obliquely out from the trial base body 735. In accordance with the illustrated embodiment, the track 773 extends out from the collars of the trial base body 735 in a direction angularly offset with respect to both the lateral and the transverse directions.

Thus, the track 773 is laterally offset with respect to a laterally central midline of the endplates 750 and 752. It should be appreciated that the track can extend along a direction having an upper transverse directional component, or a downward transverse directional component. It should be further appreciated that the trial base can include more than one track 773 extending out from the trial base body, each having an upper transverse directional component or a downward transverse directional component. The guide body channel 792 is configured to receive a select one of the at least one track 773 of the trial base 734 before the shaft 724 rotatably engages the trial base 734.

The guide body channel 792 defines a cross sectional dimension that is substantially equal to or slightly greater than that of the track or tracks 773. Accordingly, the track or tracks 773 are configured to ride within and translate within the channel 792 as the shaft 724 is rotated relative to the trial base 734, thereby causing the trial implant 722 to translate relative to the shaft 724 in the manner described above.

The stop 780 further defines a vertebral abutment surface 727 defined by the distal surface of the guide body 785. Thus, the vertebral abutment surfaces 727 is configured to abut the vertebrae that is aligned with the track 773 that is received in the channel 792 or otherwise engages the guide body 785. For instance, if the guide body 785 engages a track 773 that has an upper transverse directional component, the vertebral abutment surface 727 can abut the superior vertebra. If the guide body 785 engages a track 773 that has a downward transverse directional component, the vertebral abutment surface 727 can abut the inferior vertebra. It should be appreciated that the stop 780 could include a pair or a plurality of guide members 785, each configured to engage a track 773 of the trial base 734 as desired.

Referring now to FIGS. 17A-B, a trial implant assembly 820 constructed in accordance with an alternative embodiment is illustrated including reference numerals corresponding to like elements of the trial implant assembly 20 incremented by 800. Thus, the trial implant assembly 820 can be constructed substantially as described with respect to the trial implant assembly 20 except as otherwise noted. As illustrated, the trial implant assembly 820 includes a shaft 824 and a trial implant 822 configured to be removably coupled to the shaft 824. The trial implant 822 includes a trial head 836 having a superior endplate 850 and an inferior endplate 852 configured to be inserted into an intervertebral space, a trial base 834 configured to be coupled to the shaft 824, and a laterally central rib 838 connected between the trial base 834 and the trial head 836. It should be appreciated, however, that the trial base 834 could be connected directly to the trial head 836.

In particular, the rib 838 is connected between the distal end of the trial base 834 and one of the endplates 850 and 852 of the trial head 836. As illustrated, the rib 838 is connected to the inferior endplate 852, and is not connected between the endplates 850 and 852. The trial head 836 includes a pair of laterally outer endplate walls 888 that are connected between the endplates 850 and 852, such that an enclosed visualization window 860 is defined between the outer endplate walls 888 and the inner transverse surfaces 855 and 857 of the endplates 850 and 852. The trial base 834 is vertically offset from the visualization window 860.

Referring now to FIGS. 18A-B, a trial implant assembly 920 constructed in accordance with an alternative embodiment is illustrated including reference numerals corresponding to like elements of the trial implant assembly 820 incremented by 100. Thus, the trial implant assembly 920 can be constructed substantially as described with respect to the trial implant assembly 820 except as otherwise noted. As illustrated, the trial implant assembly 920 includes a shaft 924 and a trial implant 922 configured to be removably coupled to the shaft 924. The trial implant 922 includes a trial head 936 having a superior endplate 950 and an inferior endplate 952 configured to be inserted into an intervertebral space, a trial base 934 configured to be coupled to the shaft 924, and a rib 938 that is central with respect to trial base 934 connected between the trial base 934 and the trial head 936. It should be appreciated, however, that the trial base 934 could be connected directly to the trial head 936.

In particular, the rib 938 is connected between the distal end of the trial base 934 and one of the laterally outer endplate walls 988 that are connected between the endplates 950 and 952, such that an enclosed visualization window 960 is defined between the outer endplate walls 988, and further defined by the inner transverse surfaces 955 and 957 of the endplates 950 and 952. The trial base 934 is laterally offset from the visualization window 960.

It should be appreciated that the trial implants 822 and 922 illustrate that trial implants usable in connection with any of the trial implant assemblies described herein can be configured so as to provide a range of numerous possible geometries and configurations of visualization windows. The visualization windows as described herein can be rectangular, square, round, elliptical in shape, and can be geometrically regular or irregular, and may be centered with respect to the trial head or offset with respect to the trial head. The windows can further be open or enclosed.

While the trial implant instrument assemblies of the present invention have been described in reference to surgical procedures for replacing a damaged intervertebral disc with a total disc replacement implant, it is understood that the teachings of the present invention are easily configurable for surgical procedures for fusing a damaged disc space using an interbody spacer.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure.

We claim:

1. A trial implant assembly comprising:
    a trial implant including:
        a trial base including an engagement member configured to couple the trial implant to a shaft; and
        a trial head configured to be inserted into an intervertebral space defined by a superior vertebral body and an inferior vertebral body, the trial head supported by the trial base and extending distally relative to the trial base along a longitudinal direction, the trial head defining a superior endplate having an upper surface and a lower surface, and an inferior endplate having an upper surface and a lower surface, the upper surface of the superior endplate and the lower surface of the inferior endplate are spaced from each other along a transverse direction that is substantially perpendicular to the longitudinal direction, and the upper surface of the superior end plate and lower surface of the inferior endplate are configured to face the superior vertebral body and the inferior vertebral body, respectively, the trial head further defining a proximal terminal end and a distal terminal end spaced from the proximal terminal end along the longitudinal direction, the trial head further defining at least one visualization window extending through the trial head in the longitudinal direction between the superior and inferior endplates from the proximal terminal end to the distal terminal end of the trial head, wherein the at least one visualization window is defined in the transverse direction from the proximal terminal end to the distal terminal end of the trial head by the lower surface of the superior endplate and the upper surface of the inferior endplate, and a central axis of the engagement member is offset with respect to a central axis of the trial head along the transverse direction so as to allow for unobstructed visualization in the longitudinal direction through the at least one visualization window as the trial head is inserted into the intervertebral space; and the shaft, wherein the shaft has an engagement member configured to mate with the engagement member of the trial base so as to removably couple the shaft to the trial implant and the shaft extends in a direction parallel to the endplates when the shaft is coupled to the trial implant.

2. The trial implant assembly as recited in claim 1, wherein the trial base comprises a pair of spaced engagement members, each engagement member configured to be coupled to the shaft.

3. The trial implant assembly as recited in claim 1 wherein the engagement members of the shaft and the trial base comprise threads, such that the head translates relative to the shaft as the shaft is rotated relative to the trial head.

4. The trial implant assembly as recited in claim 1, wherein the shaft defines a cannulation, and an aperture extends through the trial base, the aperture being in alignment with the cannulation such that the at least one visualization window is visually accessible through the cannulation and the aperture.

5. The trial implant assembly as recited in claim 4, wherein the aperture is configured to receive the shaft.

6. The trial implant assembly as recited in claim 4, wherein the cannulation provides a suction passageway for the removal of debris under an applied vacuum pressure.

7. The trial implant assembly as recited in claim 1, wherein the trial head is translatable with respect to the shaft between an extended position and a retracted position, such that the trial head can define a greater insertion depth in the extended position than in the retracted position.

8. The trial implant assembly as recited in claim 7, wherein the shaft carries a vertebral engagement surface configured to abut at least one of the vertebral bodies when the trial head is fully inserted in the intervertebral space.

9. The trial implant assembly as recited in claim 8, wherein the at least one vertebral abutment surface comprises a pair of spaced vertebral abutment surfaces.

10. The trial implant assembly as recited in claim 9, wherein the abutment surfaces are spaced laterally so as to abut the same vertebra.

11. The trial implant assembly as recited in claim 10, wherein the abutment surfaces are spaced transversely so as to abut the vertebral bodies that define the intervertebral space.

12. The trial implant assembly as recited in claim 8, wherein the shaft defines a shaft body, the shaft including a mechanical stop that is rotatable about the shaft body and translatably fixed on the shaft body, the stop including the vertebral abutment surface.

13. The trial implant assembly as recited in claim 12, wherein the trial base further comprises at least one track, and the mechanical stop is configured to ride along the track as the trial head is translated with respect to the shaft.

14. The trial implant assembly as recited in claim 13, wherein the trial base further comprises a pair of tracks spaced from each other.

15. The trial implant assembly as recited in claim 13, wherein the trial base further comprises a pair of tracks separated by a channel, and the mechanical stop is configured to translate in the channel.

16. The trial implant assembly as recited in claim 13, wherein the trial base comprises a trial base body, and the track extends obliquely out from the trial base body.

17. The trial implant assembly as recited in claim 13, wherein the stop comprises a guide body, a channel extends into the guide body, and the track is configured to be disposed in the channel.

18. The trial implant assembly as recited in claim 13, wherein the trial base further comprises a pair of tracks that define an alignment channel configured to receive the mechanical stop, wherein the mechanical stop is configured to translate along a select one of the guide channels as the implant is translated relative to the shaft.

19. The trial implant assembly as recited in claim 13, wherein the track comprises a superior track and an inferior track, such that the stop member is configured to selectively engage the inferior vertebra or the inferior vertebra.

20. The trial implant assembly as recited in claim 1, further comprising at least one rib connected between the trial base and the trial head.

21. The trial implant assembly as recited in claim 20, wherein the at least one rib at least partially defines the at least one visualization window between the endplates.

22. The trial implant assembly as recited in claim 21, wherein the at least one rib defines a pair of visualization windows of the at least one visualization window disposed on opposed sides of the rib.

23. The trial implant assembly as recited in claim 20, wherein the at least one rib includes a pair of ribs spaced apart and connected between the superior and inferior endplates so as to at least partially define a visualization window of the at least one visualization window.

24. The trial implant assembly as recited in claim 23, wherein the visualization window is a primary visualization window, and the ribs further at least partially define a pair of auxiliary visualization windows of the at least one visualization window disposed outward of the ribs.

25. The trial implant assembly as recited in claim 24, wherein at least one of the visualization windows is enclosed.

26. The trial implant assembly as recited in claim 1, wherein the trial head includes a pair of walls extending between the upper end lower endplates, such that the at least one visualization window is defined between the walls and further between the upper and lower endplates.

27. The trial implant assembly as recited in claim 26, wherein the walls comprise ribs that are connected between the trial head and the trial base.

28. The trial implant assembly as recited in claim 1, wherein the at least one visualization window is defined by a slot that is open along a lateral direction that is substantially perpendicular to the longitudinal direction along an entirety of the length of the visualization window.

29. The trial implant assembly as recited in claim 28, wherein the visualization through the at least one visualization window is along the distal direction from a location proximal of the shaft.

30. The trial implant assembly as recited in claim 1, wherein the shaft extends proximally from the trial base, and the visualization through the at least one visualization window is along the distal direction from a location proximal of the trial head.

31. A trial implant assembly comprising:
a shaft; and a trial implant including:
- a trial base defining an engagement member configured to mate with an engagement member of the shaft so as to couple the trial base to the shaft;
- a trial head disposed distally from the trial base and configured to be inserted along a longitudinal direction into an intervertebral space defined by a superior vertebral body and an inferior vertebral body, the trial head defining a superior endplate and an inferior endplate configured to face the superior vertebral body and the inferior vertebral body, respectively, the trial head further defining a proximal terminal end and a distal terminal end spaced from the proximal terminal end along the longitudinal direction such that a length is defined from the proximal terminal end to the distal terminal end along the longitudinal direction; and
- at least one rib that extends distally from the trial base into the proximal terminal end of the trial head, the at least one rib further connected between the superior and inferior endplates so as to at least partially define a visualization window that extends through the trial head along the longitudinal direction from the proximal terminal end to the distal terminal end, and is open (i) at both the proximal and distal terminal ends between the superior and inferior end plates along the longitudinal direction, and (ii) along a lateral direction that is substantially perpendicular to the longitudinal direction along an entirety of the length such that visualization window permits unobstructed visualization therethrough along the longitudinal direction, wherein the engagement member of the shaft is threaded and the engagement member of the trial base is threaded such that the threaded engagement member of the shaft is configured to mate with the threaded engagement member of the trial base and relative rotation between the shaft and the trial base causes the trial implant to translate relative to the shaft.

32. The trial implant assembly as recited in claim 31, wherein the shaft carries a mechanical stop that is rotatable with respect to the shaft but translatably fixed with respect to the shaft, the mechanical stop defining a vertebral abutment configured to abut a select one of the vertebral bodies when the trial head is inserted into the intervertebral space.

33. A kit comprising:
- a shaft having a proximal end and an opposed distal end that defines an engagement member; and
- a trial implant including:
  - a trial head configured to be inserted into an intervertebral space defined by a superior vertebral body and an inferior vertebral body, the trial head defining a superior endplate surface and an inferior endplate surface spaced from the superior endplate surface along a transverse direction, the superior endplate surface and the inferior endplate surface being configured to face the superior vertebral body and the inferior vertebral body, respectively; the trial head further defining a proximal terminal end and a distal terminal end spaced from the proximal terminal end along a longitudinal direction;
  - a trial base defining an engagement member configured to mate with the engagement member of the shaft, such that at least a portion of the distal end of the shaft is spaced below the inferior endplate surface in the transverse direction when the engagement member of the shaft is mated with the engagement member of the trial base; and
  - at least one rib connected between the trial head and the trial base, the at least one rib further connected between the superior and inferior endplates so as to at least partially define a visualization window that extends in the longitudinal direction through the trial head, the visualization window being further defined in the transverse direction from the proximal terminal end to the distal terminal end by the superior and inferior endplates of the trial head so as to allow for unobstructed visualization through the visualization window when the shaft is coupled to the trial base and as the trial head is inserted into the intervertebral space, wherein the at least one rib is a pair of ribs that each extend from the trial head to the trial base so as to enclose the visualization window.

34. The kit as recited in claim 33, further comprising a plurality of trial implants, wherein at least some of the implants define different heights between the superior endplate surface and the inferior endplate surface than others of the implants.

35. A trial implant assembly comprising:
- a trial implant including:
  - a trial head configured to be inserted into an intervertebral space defined by a superior vertebral body and an inferior vertebral body, the trial head having a superior endplate and an inferior endplate separated vertically from the superior endplate by a gap, the superior endplate configured to face the superior vertebral body and the inferior endplate configured to face the inferior vertebral body, the trial head further defining a proximal terminal end and a distal terminal end spaced from the proximal terminal end along a longitudinal direction;
  - a trial base including an engagement member configured to couple the trial implant to a shaft; and
  - at least one rib that extends between the trial base and the trial head along the longitudinal direction, the at least one rib extending distally from the trial base into the gap between the superior endplate and the inferior endplate to a location that is distal to a midline defined between the proximal terminal end and the distal terminal end of the trial head, the at least one rib further connected between the superior and inferior endplates so as to at least partially define a boundary between a primary visualization window and a first auxiliary visualization window that is offset from the primary visualization window along a lateral direction that is perpendicular to the longitudinal direction,
  - wherein both the primary visualization window and the first auxiliary visualization window extend through the trial head between the inferior and superior endplates from the proximal terminal end to the distal terminal end so as to allow for unobstructed visualization through the trial head as the trial head is inserted into the intervertebral space.

36. The trial implant assembly as recited in claim 35, wherein the at least one rib comprises first and second ribs, the first rib defining the boundary between the primary visualization window and the first auxiliary visualization window, and the second rib defining a second boundary between the primary visualization window and a second auxiliary visualization window that is offset from the primary visualization window along the lateral direction.

37. The trial implant assembly as recited in claim 36, wherein a length is defined from the proximal terminal end to the distal terminal end, and the first and second auxiliary visualization windows are open along the lateral direction along an entirety of the length.

\* \* \* \* \*